US010858414B2

(12) United States Patent
Nuijens et al.

(10) Patent No.: US 10,858,414 B2
(45) Date of Patent: Dec. 8, 2020

(54) CHEMO-ENZYMATIC SYNTHESIS OF SEMAGLUTIDE, LIRAGLUTIDE AND GLP-1

(71) Applicant: ENZYPEP B.V., Geleen (NL)

(72) Inventors: Timo Nuijens, Geleen (NL); Ana Toplak, Geleen (NL); Peter Jan Leonard Mario Quaedflieg, Geleen (NL)

(73) Assignee: ENZYPEP B.V., Geleen (NL)

( * ) Notice: Subject to any disclaimer, the term of this patent is extended or adjusted under 35 U.S.C. 154(b) by 0 days.

(21) Appl. No.: 16/349,106

(22) PCT Filed: Mar. 8, 2019

(86) PCT No.: PCT/EP2019/055918
§ 371 (c)(1),
(2) Date: May 10, 2019

(87) PCT Pub. No.: WO2019/170895
PCT Pub. Date: Sep. 12, 2019

(65) Prior Publication Data
US 2020/0262886 A1    Aug. 20, 2020

(30) Foreign Application Priority Data

Mar. 9, 2018  (EP) .................................... 18161081

(51) Int. Cl.
*C07K 14/605* (2006.01)
*C12N 9/54* (2006.01)

(52) U.S. Cl.
CPC .............. *C07K 14/605* (2013.01); *C12N 9/54* (2013.01); *C12Y 304/21062* (2013.01); *C07K 2319/21* (2013.01)

(58) Field of Classification Search
CPC .............. C07K 14/605; C07K 2319/21; C12Y 304/21062; C12N 9/54
See application file for complete search history.

(56) References Cited

U.S. PATENT DOCUMENTS

| 5,403,737 | A | 4/1995 | Abrahmsen |
| 6,451,974 | B1 | 9/2002 | Hansen |
| 2017/0305963 | A1* | 10/2017 | Quaedflieg ............ C07K 1/026 |

FOREIGN PATENT DOCUMENTS

| WO | 0226956 | A1 | 4/2002 |
| WO | 2007147816 | A1 | 12/2007 |
| WO | 2014199397 | A2 | 12/2014 |
| WO | 2016046753 | A1 | 3/2016 |
| WO | 2016056913 | A1 | 4/2016 |
| WO | 2017007324 | A1 | 1/2017 |
| WO | 2018032843 | A1 | 2/2018 |

OTHER PUBLICATIONS

International Search Report and Written Opinion for Corresponding International Application No. PCT/EP2019/055918 (14 Pages) (dated Apr. 16, 2019).
Matsunaga et al., "Development of an Efficient Amino Acid Sequencing Method Using Fluorescent Edman Reagent 7·[( N, N-Dimethylamino)sulfonyl]-2,1,3-benzoxadiazol-4-yl Isothiocyanate", Anal. Chem., 1995, vol. 67, pp. 4276-4282.
Nuijens et al., "Chemo-enzymatic peptide synthesis (CEPS) using omniligases and selective peptiligases Efficient biocatalysts for assembling linear and cyclic peptides and protein conjugates", Chimica Oggi, 2016, vol. 34, No. 6, pp. 16-19.
Nuijens et al., "Engineering a Diverse Ligase Toolbox for Peptide Segment Condensation", Adv. Synth. Catal., 2016, vol. 358, No. 24, pp. 4041-4048.
International Search Report for Corresponding International Application No. PCT/EP2019/056046(dated Apr. 12, 2019) (20 Pages).
"Mutant subtilisin BPN' protein S88 S188P", DATABASE Geneseq, 2002, XP002790242, 1 page.
Chang et al., "Subtiligase: A tool for semisynthesis of proteins", Proc. Natl. Acad. Sci., 1994, vol. 91, pp. 12544-12548.

* cited by examiner

*Primary Examiner* — Sudhakar Katakam
(74) *Attorney, Agent, or Firm* — Lucas & Mercanti, LLP

(57) ABSTRACT

The invention relates to a method for preparing a coupling product having the sequence $P_q$-$W_v$-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly. The method includes enzymatically coupling
  (a) a peptide C-terminal ester or thioester having a first peptide fragment represented by the formula $P_q$-$W_v$-His-X-Glu-(thio)ester; and
  (b) a peptide nucleophile having an N-terminally unprotected amine having a second peptide fragment with the sequence  H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly
wherein
  P represents a protective group at the N-terminal α-amino function of the peptide C-terminal ester or thioester and q is an integer having a value of 1 or 0;
  W represents one or more amino acid residues, which may be the same or different and v is an integer having a value of 1 or more representing the number of amino acid residues W;
  X is Ala or an α-amino-isobutyric acid unit (Aib);
  Y is Lys, which Lys has a free side-chain ε-amino group or a side-chain ε-amino group that is protected with a protective group or a side-chain ε-amino group that is functionalized with an amino acid or another functional group; and
  Z is Arg or Lys.

20 Claims, No Drawings
Specification includes a Sequence Listing.

CHEMO-ENZYMATIC SYNTHESIS OF SEMAGLUTIDE, LIRAGLUTIDE AND GLP-1

CROSS-REFERENCE TO RELATED APPLICATIONS

This application is a 371 of PCT/EP2019/055918, filed Mar. 8, 2019, which claims the benefit of European Patent Application No. 18161081.7, filed Mar. 9, 2018.

FIELD OF THE INVENTION

The invention relates to a method wherein a peptide fragment coupling is carried out enzymatically in the presence of a ligase to synthesise a peptide comprising the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly.

BACKGROUND OF THE INVENTION

Several peptides comprising the amino acid sequence H-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly-OH are well known in the art as insulinotropic peptides. These peptides include GLP-1, Liraglutide and Semaglutide.

Human GLP-1 (Glucagon-like peptide-1) has the formula H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-OH.

Liraglutide is an $Arg^{20}$-GLP-1 analogue substituted on the ε-amino group of the lysine in position 20 of the above sequence with a Glu-spaced palmitic acid. Thus Liraglutide has the formula H-His-Ala-Glu-Gly-Thr-Phe-Thr-Ser-Asp-Val-Ser-Ser-Tyr-Leu-Glu-Gly-Gln-Ala-Ala-Lys(Pal-γ-Glu)-Glu-Phe-Ile-Ala-Trp-Leu-Val-Arg-Gly-Arg-Gly-OH (see also FIG. 1, all chiral amino acid residues are L-amino acid residues). In Lys(Pal-γ-Glu) the ε-amino-group of the Lys residue is linked with the γ-Glu carboxylic side-chain and the Glu is N-palmitoylated.

Semaglutide has the formula H-His-Aib-Glu-Gly-Thr-Phe-Thr-Ser-Asp-Val-Ser-Ser-Tyr-Leu-Glu-Gly-Gln-Ala-Ala-Lys(AEEA-AEEA-γ-Glu-17-carboxyheptadecanoyl)-Glu-Phe-Ile-Ala-Trp-Leu-Val-Arg-Gly-Arg-Gly-OH. Herein Aib is an α-amino-isobutyric acid residue and AEEA-AEEA-γ-Glu-17-carboxyheptadecanoyl is N-(17-carboxy-1-oxoheptadecyl)-L-γ-glutamyl-2-[2-(2-aminoethoxy)ethoxy]acetyl (see also FIG. 2, all chiral amino acid residues are L-amino acid residues).

These peptides can, e.g., be used in the treatment of diabetes II. Further, e.g., Liraglutide can be used in the treatment of obesity, as injectable adjunct to a reduced-calorie diet and increased physical activity for chronic weight management in adult patients.

Processes for synthesizing peptides, including oligopeptides like GLP-1, Liraglutide and Semaglutide, are known in the art. Methods to synthesise insulinotropic peptides, such as GLP-1 and analogues thereof are described in WO2007147816 and in WO2016/046753. GLP-1, which is a naturally occurring peptide, can be produced fermentatively, i.e. in biological cells, e.g. in yeast cells, through recombinant gene technology (see e.g. WO2016/046753). Use of a fermentative production of insulinotropic peptides on a large scale has advantages. However, this technology also has limitations with respect to the peptides that can be produced on an industrial scale in practice. It is for example a challenge, if possible at all, to fermentatively produce peptides comprising a non-proteinogenic amino acid in their amino acid sequence. For instance, the amino acid sequence of Semaglutide comprises an α-amino-isobutyric acid (Aib) residue, which is non-proteinogenic.

Further, GLP-1 analogues, like Semaglutide and Liraglutide, are functionalised at a side-chain group of an amino acid in their sequence. In the case of Semaglutide and Liraglutide the side-chain ε-amino group of $Lys^{20}$ has been functionalized. This functionalization of the side-chain needs to be done by chemical means. When coupling chemically, it may be difficult to discriminate between the N-terminal α-amino function and the side-chain function at which functionalization is desired, e.g. if a carboxylic acid is to be coupled to the α-amino function of the Glu of a $Lys^{20}$(γ-Glu-OH) side-chain. Further, when preparing Semaglutide, one should consider that the AEEA-AEEA-γ-Glu-17-carboxyheptadecanoyl moiety to be coupled to the amino acid sequence of Semaglutide has three different carboxylic acid functionalities, of which only the γ-Glu carboxylic acid needs to be coupled. Protecting group strategies are needed. After coupling of the activated (optionally protected) AEEA-AEEA-γ-Glu-17-carboxyheptadecanoyl a peptide fragment containing the Aib residue should be coupled to the N-terminus. This is usually performed between position 4 and 5, i.e. by coupling of the peptide with amino acid residues 1-4+the peptide with amino acid residues 5-31, because no racemization occurs when activating $Gly^4$. The 1-4 peptide should be protected at the N-terminus as well as at least at the side chain functionality of $^3$Glu to avoid side-reactions (e.g. polymerization). Combining fermentation of an unprotected peptide with chemical coupling of protected peptides is a challenge since solubility of the two is very different (water vs. organic solvents). After the chemical condensation reaction the protecting groups should be removed, leading to a multi-step synthesis strategy.

In the 'BACKGROUND OF THE INVENTION' of WO2016/046753 a detailed description is given of suitable preparation methods, notably recombinant methodology, sequential synthesis on a solid support, solid phase synthesis of Liraglutide involving coupling a peptide sequence containing amino acid residues (1-10) to a sequence containing amino acid residues (11-31), or solid phase synthesis of Liraglutide involving the preparation of peptide sequences containing amino acid residues (1-4), (15-16) and (17-31), coupling the peptides containing amino acid residues (15-16) with (17-31) and sequential addition of amino acids before coupling with the peptide containing amino acid sequence (1-4). In accordance with WO2016/046753 GLP-1 peptides are prepared in a process comprising liquid or solid phase peptide synthesis or a combination thereof, wherein the process comprises a final coupling step in which fragments are coupled at a terminal Gly residue, and wherein at least one of the fragments is prepared by coupling of at least two sub-fragments. Liraglutide is in particular obtained by coupling His-Ala-Glu-Gly and Thr-Phe-Thr-Ser-Asp-Val-Ser-Ser-Tyr-Leu-Glu-Gly-Gln-Ala-Ala-Lys(Pal-Glu-OX)-Glu-Phe-Ile-Ala-Trp-Leu-Val-Arg-Gly-Arg-Gly-OH. In this sequence X represents H or a protecting group for the Glu α-carboxylic acid group.

As follows from 'BACKGROUND OF THE INVENTION' of WO2016/046753 there remains a need for discovering new methods for the synthesis of GLP-1 and GLP-like peptides such as Liraglutide or Semaglutide to provide a better, more efficient and cheaper process or to provide a product which can be more readily purified in order to achieve a product with improved yield and purity. In particular, it expresses the need to provide a method for preparing GLP-1 and analogues, such as Liraglutide or Semaglutide, especially on an industrial scale, which should not require the use of toxic or otherwise undesirable reagents in good yields and which can be readily purified to obtain a product having high purity.

A chemo-enzymatic synthesis of GLP-1 or an analogue thereof, like Liraglutide or Semaglutide is not suggested in WO2007147816 nor in WO2016/046753, which both focus on fully chemical synthesis.

However, fully chemical synthesis of peptides has disadvantages, as also discussed in the above cited prior art.

In contrast to chemical couplings, enzyme-catalysed peptide couplings are completely devoid of racemisation and have several other advantages over chemical peptide synthesis such as the absence of side reactions on the side-chain functionalities during the coupling process. For industrial application, an enzymatic peptide synthesis concept based on a kinetic approach, i.e. using an acyl donor C-terminal ester is most attractive (see for instance N. Sewald and H.-D. Jakubke, in: "Peptides: Chemistry and Biology", 1st reprint, Ed. Wiley-VCH Verlag GmbH, Weinheim 2002).

A problem with enzymatic coupling in aqueous solutions is that the presence of water tends to promote hydrolysis rather than coupling. Some reports have been published on the enzymatic condensation of oligopeptide fragments in aqueous solution (Kumaran et al. Protein Science, 2000, 9, 734; Bjorup et al. Bioorg. Med. Chem. 1998, 6, 891; Homandberg et al. Biochemistry, 1981, 21, 3387; Komoriya et al. Int. J. Pep. Prot. Res. 1980, 16, 433).

It was found by Wells et al. (U.S. Pat. No. 5,403,737) that the enzymatic condensation of oligopeptides in aqueous solution could be significantly improved by altering the active site of subtilisin BPN', a subtilisin from *Bacillus amyloliquefaciens* (SEQUENCE ID NO: 2). When two mutations were introduced, i.e. S221C and P225A, a subtilisin BPN' variant called subtiligase was obtained having a 500-fold increased synthesis over hydrolysis ratio (S/H ratio) as compared to wild-type subtilisin BPN'. In further experiments Wells et al. added five additional mutations to subtiligase to make the enzyme more stable (Proc. Natl. Acad. Sci. USA, 1994, 91, 12544). The new mutant called stabiligase appeared moderately more resistant to sodium dodecasulphate and guanidinium hydrochloride, but hydrolysis was still a major side reaction.

In WO 2016/056913 a solution is provided for the undesirably high hydrolytic activity encountered with enzymes like subtiligase or stabiligase when used for (oligo)peptide synthesis in an aqueous environment, by providing subtilisin BPN' variants or a homologues thereof, with specific mutations. These variants or homologues are in particular suitable to catalyse the synthesis of peptides by coupling a first peptide fragment and a second peptide fragment, wherein the first fragment is a peptide C-terminal ester or thioester and the second fragment is a peptide nucleophile having an N-terminally unprotected amine.

The inventors considered to apply enzymatic fragment condensation to synthesise GLP-1, Liraglutide and Semaglutide starting from peptide fragments mentioned in WO2007147816 or WO2016/046753, such as by enzymatically coupling a peptide C-terminal (thio)ester having amino acid residues 1-10 to a peptide nucleophile containing amino acid residues 11-31 of liraglutide, semaglutide or GLP-1 or by enzymatically coupling a peptide C-terminal (thio)ester having amino acid residues 1-4 to a peptide nucleophile containing amino acid residues (5-31) of Liraglutide, Semaglutide or GLP-1. They further contemplated that at least the relatively long nucleophile could then efficiently be prepared fermentatively if desired, after which the relatively short thio(ester), which may comprise the non-proteinogenic Aib would be coupled enzymatically with the nucleophile.

However, they concluded this to be ineffective. For the coupling of the peptide C-terminal (thio)ester having amino acid residues 1-10 to a peptide nucleophile containing amino acid residues 5-31, one of the reasons was considered to be the presence of a serine at both P1' and P2', which the inventors found to be a disadvantage for the peptide nucleophile. Further possible reasons for a lack of effective coupling could be the presence of a non-hydrophobic amino acid at P4 (threonine) of the peptide C-terminal (thio)ester. For the coupling of the peptide C-terminal (thio)ester having amino acid residues 1-4 to a peptide nucleophile containing amino acid residues 5-31, the inventors concluded that in particular the presence of a histidine at P4 and/or the presence of glycine at P1 of the peptide C-terminal (thio) ester are detrimental to effective coupling. The inventors found that it is possible to prepare peptides like GLP-1, Liraglutide and Semaglutide by enzymatic coupling in the presence of a ligase, also in an aqueous reaction medium, but that the yield was unexpectedly low for several processes designed on the basis of scientific considerations, such as the consideration that a ligase like a subtilisin variant or homologue thereof favours coupling of C-terminal peptide (thio) esters that have a hydrophobic amino acid residue at the S4 position (the fourth amino acid from the C-terminal end) of the peptide C-terminal ester or thioester.

Amongst others, attempts were made to enzymatically prepare the amino acid sequence of Semaglutide from the corresponding 3-mer C-terminal ester and the 28-mer peptide nucleophile, from the corresponding 4-mer C-terminal ester and the 27-mer peptide nucleophile, from the corresponding 5-mer C-terminal ester and the 26-mer peptide nucleophile and from the corresponding 6-mer C-terminal ester and the 25-mer peptide nucleophile. These attempts were not successful. For the enzymatic coupling of the 4-mer and the 27-mer this was expected, in view of the presence of the non-proteinogenic Aib at a relevant position for enzyme recognition, namely the P3 position (the third amino acid from the C-terminal end), but the 5-mer+26-mer fragments and the 6-mer+25-mer fragments had been considered promising fragments to be coupled in the presence of a ligase (see also Example 7).

SUMMARY OF THE INVENTION

It is an object of present invention to provide a novel method of enzymatically synthesizing GLP-1 or an analogue thereof, in particular Semaglutide or Liraglutide. There is a need for alternative enzymatic peptide synthesis processes for these peptides in general, in particular in order to broaden the palette of tools for making them. In particular it is an object of present invention to provide such a process that overcomes one or more of the problems mentioned above or discussed in the above cited prior art, more in particular an improved overall yield or an improved selectivity.

One or more other objects that may be subject of the invention follow from the description below.

It has now surprisingly been found that one or more of these objects are met by a method wherein GLP-1 or an analogue thereof is prepared in a method comprising the enzymatic synthesis of a peptide by fragment condensation, wherein two specific peptide fragments are coupled in the presence of a ligase, in particular a subtilisin variant or homologue.

Accordingly, the present invention relates to a method for preparing a coupling product comprising the sequence $P_q$-$W_v$-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly, comprising enzymatically coupling (a) a peptide C-terminal ester or thioester comprising a first peptide fragment represented by the formula $P_q$-$W_v$-His-X-Glu-(thio)ester; and (b) a peptide nucleophile having an N-terminally unprotected amine comprising a second peptide fragment comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly wherein
  P represents a protective group at the N-terminal α-amino function of said peptide C-terminal ester or thioester and q is an integer having a value of 1 or 0;
  W represents one or more α-amino acid residues, which may be the same or different and v is an integer having a value of 1 or more representing the number of α-amino acid residues W;
  X is Ala or an α-amino-isobutyric acid unit (Aib);
  Y is Lys, which Lys has a free side-chain ε-amino group or a side-chain ε-amino group that is protected with a protective group or a side-chain ε-amino group that is functionalised with an amino acid or another functional group, in particular a functional group selected from the group consisting of γ-Glu-OH, Pal-γ-Glu-OH, AEEA-AEEA-γ-Glu-OH and AEEA-AEEA-γ-Glu-N-17-carboxyheptadecanoyl-OH,
    wherein Pal is palmitoyl and AEEA-AEEA is 2-[2-(2-aminoethoxy)ethoxy]acetyl-2-[2-(2-aminoethoxy)ethoxy]acetyl;
  Z is Arg or Lys;
which enzymatic coupling is catalysed by a ligase.

Accordingly, in a specific embodiment, the method of the invention further comprises removing the '$P_q$-$W_v$' moiety from the product comprising the sequence Pq-Wv-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly such as to obtain a peptide with the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly, wherein P, q, v, W, X, Y, and Z are as defined above.

Therefore, the method according to the invention is in particular suitable in the synthesis of coupling products from which biologically active peptides like the peptide sequences for Semaglutide or Liraglutide, Semaglutide as such, Liraglutide as such, can be obtained by removal of $P_q$-$W_v$.

Accordingly, the invention further relates to a method for synthesising a peptide comprising the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly, wherein, from the coupling product comprising the sequence $P_q$-$W_v$-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly obtained in the method according to the invention, and wherein P, q, v, W, X, Y, and Z are as defined above for said method, the '$P_q$-$W_v$' moiety is removed and the peptide comprising the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly is obtained.

The removal of '$P_q$-$W_v$' moiety is usually accomplished by an Edman-type reaction, wherein P is an Edman-type protective group and amino acid residues W are removed one by one (as a P-W) by subsequent coupling of a group P to the N-terminal W and cleaving off of a group P-W, see below for further details.

The present invention allows the synthesis of the peptide of interest in a high yield. Purification is relatively easy and a high purity of the peptide is feasible. It is in particular surprising that a method according to the invention allows the enzymatic synthesis of the peptide of interest (the ligation product) in a high yield, also when carried out in an aqueous reaction medium, in view of the unsatisfactory results with the enzymatic coupling of other fragments.

This has been accomplished without needing any side-chain protective groups on the peptide fragments, and without needing one or both of the fragments to be provided with a functional group to increase solubility (e.g. a 2-hydroxy-4-methoxybenzyl amide group on the peptide backbone amide functionality or a peptide-tag of polar amino acids at the terminal ends of the respective fragments not taking part in the coupling reaction), although in a specific embodiment use may be made of protective groups or solubility-enhancing groups. The high S/H ratio without needing a solubility-enhancing group is surprising because the solubility of the peptide nucleophile is very low.

The invention is also advantageous in that it allows the production of the (4-31)-mer peptide nucleophile fermentatively, after which it can conveniently be coupled with the C-terminal peptide (thio)ester. In case the 'Y' of the final peptide product needs have a functionalized ε-amino group, such as to synthesize Semaglutide or Liraglutide, the functionalization can be provided to the peptide nucleophile prior to the enzymatic coupling, or thereafter.

It is in particular surprising that a method according to the invention allows the synthesis of the peptide of interest (the ligation product) in a high yield, even when the amino acid residue at the P2 position (X) is an Aib. After all, this is a non-proteinogenic α,α-dialkyl amino acid and it is surprising that the presence of this amino acid at a crucial position for substrate recognition by a ligase, such as a subtilisin or variant or homologue thereof, does not adversely affect the coupling.

It is further an advantage of the invention that it offers flexibility in peptide synthesis in that the amino acid sequence of the peptide nucleophile needed both for Semaglutide and for Liraglutide in a method of the invention is the same. Thus, one can prepare a stock of peptide nucleophile of which part can be used for the production of Semaglutide and part for the production of Liraglutide. Thus, a single fermentation reaction system suffices for the production of both products. Further, in a process wherein a peptide fragment is prepared fermentatively prior to enzymatic coupling, the preparation of the fragment is generally the limiting step. Thus, the ability to keep one stock nucleophile for both the preparation of Semaglutide and Liraglutide, which can be synthesised relatively fast from that stock nucleophile, adds to flexibility in that one can quickly adapt the product volumes in response to changes in demand for one or the other product.

Coupling with a peptide nucleophile wherein Y is a Lys of which the side-chain ε-amino group has been functionalised with an amino acid or another functional group has in particular been found possible with subtilisin BPN' variants, as described in further detail elsewhere herein. Preferred embodiments of methods wherein the coupling is carried out using a peptide nucleophile wherein Y is a Lys of which the side-chain ε-amino group is functionalised will also be described in further detail below.

DETAILED DESCRIPTION OF THE INVENTION

For the purpose of this invention, with "synthesis over hydrolysis ratio" (S/H ratio) is meant the amount of enzymatically synthesised (oligo)peptide product divided by the amount of (oligo)peptide C-terminal ester or thioester of which the ester or thioester group has been hydrolysed. For further details on determining an S/H ratio, reference is made to WO 2016/056913.

The term "or" as used herein is defined as "and/or" unless it is specified otherwise or it follows from the context that it means 'either . . . or . . . '.

The term "a" or "an" as used herein is defined as "at least one" unless it is specified otherwise or it follows from the context that it should refer to the singular only.

When referring to a noun (e.g. a compound, an additive, etc.) in the singular, the plural is meant to be included, unless it follows from the context that it should refer to the singular only.

The term 'pH' is used herein for the apparent pH, i.e. the pH as measured with a standard, calibrated pH electrode.

For the purpose of this invention, with "peptides" is meant any chain composed of two or more amino acids. Thus, peptides are generally amides at least conceptually composed of two or more amino carboxylic acid molecules (i.e. amino acids) by formation of a covalent bond from the carbonyl carbon of one to the nitrogen atom of another with formal loss of water. The term 'peptide' is usually applied to structures formed from α-amino acids, although a peptide may comprise other amino acids, such as one or more beta-amino acids and/or one or more γ-amino acids.

The term "peptide fragment" or "fragment" refers to a peptide with a partial amino acid sequence, with reference to a longer peptide with a defined sequence. The amino acid sequence of a peptide is referred to as the primary structure. In an embodiment, the peptide is essentially free of a secondary structure and essentially free of a tertiary structure.

In an embodiment, a peptide that has been synthesised or that is to be coupled in a method according to the invention essentially consists of amino acid residues. E.g. GLP-1 consists of amino acid residues. In a further embodiment, the peptide essentially consists of amino acid units and protective groups.

In a further embodiment, a peptide that has been synthesised or that is to be coupled in a method according to the invention is a conjugate of a peptide chain and another residue, such as a fatty acid. These peptides are called lipopeptides. Fatty acids can e.g. be used to change the solubility. Examples of suitable fatty acids, are C8-C24 saturated fatty acids and C8-C24 unsaturated fatty acids. If desired, a polar linker is provided between the peptide and the fatty acid, e.g. to increase the solubility in an aqueous environment. Liraglutide and Semaglutide are peptides that are conjugates of a peptide chain and a fatty acid. Semaglutide comprises a polar linker between the peptide and the fatty acid residue.

Typically, peptides—which term includes oligopeptides, proteins and chimeric peptides—comprise up to about 35 000 amino acid units, in particular. 3-20 000, more in particular 4-1000 or 5-500 amino acid units. The ligase according to the invention may be used for the synthesis of other peptides than His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly. Such peptide preferably comprises 500 amino acid units or less, in particular 200 or less, more in particular 100 or less. In a specifically preferred embodiment, the synthesised peptide comprises at least 10 amino acid units, more specifically at least 15 amino acids, at least 25 amino acids or at least 40 amino acids. The fragments from which such peptide can be chosen within wide ranges; the length of a fragment can be at least 2, in particular at least 5, more in particular at least 10, with the upper limit determined by the length of the synthesised peptide.

With "oligopeptides" is meant within the context of the invention, a peptide composed of 2-200 amino acid units, in particular composed of 5-100 amino acid units, more in particular composed of 10-50 amino acid units.

For the purpose of this invention, with "peptide bond" is meant the amide bond between (i) either the α-amino terminus of one α-amino acid or the beta-amino terminus of one beta-amino acid and (ii) either the α-carboxyl terminus of one other α-amino acid or the beta-carboxyl terminus of one other beta-amino acid. Preferably, the peptide bond is between the α-amino terminus of one α-amino acid and the α-carboxyl terminus of another α-amino acid.

In the context of the invention with "amino acid side-chain" is meant any proteinogenic or non-proteinogenic amino acid side-chain.

Proteinogenic amino acids are the amino acids that are encoded by the genetic code. Proteinogenic amino acids include: alanine (Ala), valine (Val), leucine (Leu), isoleucine (Ile), serine (Ser), threonine (Thr), methionine (Met), cysteine (Cys), asparagine (Asn), glutamine (Gln), tyrosine (Tyr), tryptophan (Trp), glycine (Gly), aspartic acid (Asp), glutamic acid (Glu), histidine (His), lysine (Lys), arginine (Arg), proline (Pro) and phenylalanine (Phe). Selenocysteine (Sec, U) is an amino acid, of which the structure corresponds to cysteine, with the proviso that it contains a selenium instead of a sulphur atom. Proteinogenic amino acids are the L-stereoisomers of said amino acids (except for glycine, which does not have a stereo-isomeric form).

The non-proteinogenic amino acid of particular interest in a method according to the present invention is 2-aminoisobutyric acid (Aib), which forms part of the peptide chain of Semaglutide.

The term "(thio)ester" is used herein as short-hand for the phrase "ester or thioester".

The term "N-terminal protection" is used herein to indicate that an N-terminal amine group of a peptide, typically the N-terminal α-amine group, is provided with a protective group, generally at least substantially protecting the N-terminal amine group from being coupled to a C-terminal carboxylic group of another peptide or of the same peptide molecule.

The term "C-terminal protection" is used herein to indicate that a C-terminal carboxylic group of a peptide, typically the C-terminal α-carboxylic group is provided with a protective group, generally substantially protecting the carboxylic group from being coupled to an N-terminal amine group of another peptide or of the same peptide molecule.

The term "mutated" or "mutation" as used herein regarding proteins or polypeptides—in particular enzymes such as ligases—means that at least one amino acid in the wild-type or naturally occurring protein or polypeptide sequence has been replaced with a different amino acid, inserted into, appended to, or deleted from the sequence via mutagenesis of nucleic acids encoding these amino acids. Mutagenesis is a well-known method in the art, and includes, for example, site-directed mutagenesis by means of PCR or via oligo-nucleotide-mediated mutagenesis as described in Sambrook et al., Molecular Cloning-A Laboratory Manual, 2nd ed., Vol. 1-3 (1989). The term "mutated" or "mutation" as used herein regarding genes means that at least one nucleotide in the nucleic acid sequence of that gene or a regulatory sequence thereof, has been replaced with a different nucleotide, has been inserted into, has been appended to, or has been deleted from the sequence via mutagenesis, resulting in the transcription of a protein sequence with a qualitatively of quantitatively altered function or resulting in the knock-out of that gene.

In the present specification, a shorthand for denoting amino acid substitutions employs the single letter amino acid code of the amino acid that is substituted, followed by the number designating where in the protein amino acid sequence the substitution is made. This number is the amino acid position of the wild-type amino acid sequence. Thus for the mutated amino acid sequence it is the amino acid position corresponding to the position with that number in the wild type enzyme. Due to one or more other mutations at a lower position (additions, insertions, deletions, etc.) the actual position does not need to be the same. The skilled person will be able to determine the corresponding positions using a generally known alignment technique, such as NEEDLE. The number is followed by the single letter code of the amino acid that replaces the wild-type amino acid therein. For example, S221C denotes the substitution of serine at the position corresponding to position 221 to cysteine. X is used to indicate any other proteinogenic amino acid than the amino acid to be substituted. For example, S221X denotes the substitution of serine at the position corresponding to position 221 to any other proteinogenic amino acid.

The term "ligase" is used herein for an enzyme having catalytic activity in the coupling of two peptides by catalysing the formation of a peptide bond by coupling the C-terminus of a first peptide and the N-terminus of another peptide. Generally, the ligase (used in a method) according to the invention has ligase activity with respect to coupling a peptide represented by the formula $P_q$-$W_v$-His-X-Glu-(thio)ester, and a peptide nucleophile represented by the formula H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly. Therefore, in the context of the present invention a "peptide nucleophile" or a "peptide nucleophile fragment" indicates the peptide with free N-terminus participating in the enzymatically catalysed coupling, i.e. in the formation of said peptide bond. It is preferred that said ligase is a variant of the subtilisin BPN' (SEQ ID NO 2).

As defined by Schechter and Berger, the active site residues in proteases, including ligases are composed of contiguous pockets termed subsites. Each subsite pocket binds to a corresponding residue in the peptide substrate sequence, referred to here as the sequence position. According to this definition, amino acid residues in the substrate sequence are consecutively numbered outward from the cleavage sites as . . . -P4-P3-P2-P1-P1'-P2'-P3'-P4'- . . . (the scissile bond is located between the P1 and P1' positions), while the subsites (pockets) in the active site are correspondingly labelled as . . . -S4-S3-S2-S1-S1'-S2'-S3'-S4'-. (Schechter and Berger, Biochem Biophys Res Commun. 1967 Apr. 20; 27(2):157-62). It should be noted that not all proteases have all of said subsites. E.g. an S3' and/or an S4' pocket may be absent in a subtilisin BPN' variant or homologue thereof according to the invention.

For the purpose of this invention, with "S1, S2, S3 and S4 pocket" refers to the amino acids of a protease (in particular a ligase) which interact with the amino acids of a peptide acyl donor. The C-terminal amino acid ($1^{st}$ amino acid; P1) of the acyl donor peptide interacts with the amino acids in the S1 pocket of the protease. The penultimate amino acid ($2^{nd}$ amino acid from the C-terminal end; P2) of the acyl donor peptide interacts with the amino acids in the S2 pocket of the protease, the third amino acid (P3) with the S3 and the fourth amino acid (P4) with the S4 pocket. The S1-S4 binding pockets of a protease are defined by several amino acids which can be distant in the primary structure of the protease, but are close in the three dimensional space. For the purpose of this invention, with S1' and S2' pockets are meant the amino acids of a protease which interact with the N-terminal amino acids of a peptide nucleophile. The N-terminal amino acid of the peptide nucleophile interacts with the amino acids in the S1' pocket of the protease. The N-terminal penultimate amino acid of the peptide nucleophile interacts with the amino acids in the S2' pocket of the protease. The S1' and S2' binding pockets of a protease are defined by several amino acids which can be distant in the primary structure of the protease, but are close in the three dimensional space.

When an enzyme is mentioned with reference to an enzyme class (EC) between brackets, the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at http://www.chem.qmul.ac.uk/iubmb/enzyme/. Other suitable enzymes that have not (yet) been classified in a specified class but may be classified as such, are meant to be included.

Homologues typically have an intended function in common with the peptide or enzyme, of which it is a homologue, such as being capable of catalyzing the same reaction, in particular an enzymatic coupling of a method according to the invention.

Amino acid or nucleotide sequences are said to be homologous when exhibiting a certain level of similarity. Whether two homologous sequences are closely related or more distantly related is indicated by "percent identity" or "percent similarity", which is high or low respectively.

The terms "homology", "percent homology", "percent identity" or "percent similarity" are used interchangeably herein. For the purpose of this invention, it is defined here that in order to determine the percent identity of two amino acid sequences, the complete sequences are aligned for optimal comparison purposes. In order to optimise the alignment between the two sequences gaps may be introduced in any of the two sequences that are compared. Such alignment is carried out over the full length of the sequences being compared. Alternatively, the alignment may be carried out over a shorter length, for example over about 20, about 50, about 100 or more nucleic acids or amino acids. The percentage identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B.

Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, pp 443-453). The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity between the two aligned sequences is calculated as follows: the number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity". For purposes of the invention the level of identity (homology) between two sequences is calculated according to the definition of "longest-identity" as can be carried out by using the program NEEDLE.

The polypeptide sequences, in particular enzyme sequences, can further be used as a "query sequence" to perform a search against sequence databases, for example to identify other family members or related sequences. Such searches can be performed using the BLAST programs. Software for performing BLAST analyses is publicly available through the National Center for Biotechnology Information (http://www.ncbi.nlm.nih.gov). BLASTP is used for amino acid sequences. The BLAST program uses as defaults:

Cost to open gap: default=11 for proteins
Cost to extend gap: default=1 for proteins
Expect value: default=10
Wordsize: default=28 for megablast/3 for proteins Furthermore, the degree of local identity (homology) between the amino acid sequence query and the retrieved homologous sequences is determined by the BLAST program. However, only those sequence segments are compared that give a match above a certain threshold. Accordingly, the program calculates the identity only for these matching segments. Therefore, the identity calculated in this way is referred to as local identity.

The term "homologue" is used herein in particular for peptides, more in particular enzymes, having a sequence identity of at least 50%, preferably at least 60%, more preferably at least 70%, at least 80%, at least 90%, at least 95%, at least 96%, at least 97%, at least 98% or at least 99% with the peptide, in particular enzyme, with which the homologue peptide or enzyme is compared. Evidently, the sequence identity will be less than 100%. The percentage of sequence identity will depend on the number of mutations and the length of the peptide (enzyme) with which the homologue is compared. In 'longest identity' alignment deletions are not taken into account.

For the purpose of this invention, "condensation" refers to the formation of a new amide bond between the C-terminal carboxylic function of a peptide) with the N-terminal amine function of a nucleophile, in particular another peptide.

The term "analogue" of a peptide is used in particular for peptides that are structural analogues and/or functional analogues of said peptide. Functional analogues have a same in vivo target (e.g. the same target receptor on a cell membrane); structural analogues have a high similarity in amino acid sequence. Functional analogues of a peptide may have a relatively low amino acid sequence identity, e.g. of about 50% or less over the full amino acid sequence, yet a high sequence identity (and thus a high structural similarity) with the peptide of which they are an analogue in a segment of the amino acid sequence, such as near the N-terminal part or near the C-terminal part. A structural analogue, in particular comprises an amino acid sequence that has at least 60%, more in particular at least 70%, preferably at least 80%, more preferably at least 90% sequence identity, more preferably at least 95% sequence identity with the amino acid sequence of the peptide of which a peptide is an analogue. For the purpose of clarity and a concise description features are described herein as part of the same or separate embodiments, however, it will be appreciated that the scope of the invention may include embodiments having combinations of all or some of the features described. Terms used herein that are not specifically defined herein are as defined in WO 2016/056913, or—if not defined therein—used in accordance with common general knowledge.

The peptide C-terminal ester or thioester, used for the enzymatic coupling, comprises a first peptide fragment comprising the amino acid sequence -His-X-Glu-, i.e. amino acid residues 1, 2 and 3 of peptides like GLP-1, Semaglutide and Liraglutide. The α-carboxylic acid of the Glu is (thio)esterified and the α-amino group of the His is bound to an amino acid residue W via a peptidic bond via the α-carboxylic acid functionality of the amino acid residue W. The presence of the additional amino acid residue(s) $W_v$ effectively extends the 3-mer His-X-Glu to a tetramer (if v=1) or a larger peptide (if v>1). Such extension has been found important to allow effective enzymatic coupling of the peptide C-terminal ester or thioester to the peptide nucleophile. Thus, the peptide C-terminal ester or thioester used for the enzymatic coupling is represented by the formula $P_q$-$W_v$-His-X-Glu-(thio)ester. Herein X is Ala or an α-aminoisobutyric acid residue (Aib). Herein, v is an integer representing the number of amino acid residues W, having a value of at least 1, usually of 1-10, preferably 1-4, more preferably 1, 2 or 3, most preferably 1. Particularly good results have been achieved in an enzymatic coupling wherein $P_q$-W-His-X-Glu-(thio)ester is the amino acid sequence of the first peptide fragment, with q being either 0 or 1. Thus, the presence of a single amino acid residue W generally suffices for effective enzymatic coupling. If desired, one or more additional amino acid residues W can be present, e.g. to modify solubility in the reaction medium. However, this is generally not required, especially not in an aqueous reaction medium.

Each W can be the same or different. Usually each W represents a proteinogenic amino acid residue. For a particularly good enzymatic coupling, in particular when using a subtilisin variant or homologue, at least the W forming a peptidic bond with the His of His-X-Glu- is selected from the group consisting of Phe, Leu, Ile, Val, Ala, Tyr, Met, Pro and Trp. In a particularly preferred embodiment, at least the W adjacent to the His of the His-X-Glu- is a relatively large hydrophobic amino acid residue selected from the group consisting of Phe, Leu, Ile and Val. Most preferably at least said W adjacent to said His is a Phe.

In principle, for N-terminal amine protection during enzymatic coupling any protective group can be used, e.g. as described in WO 2016/056913, for instance Cbz, Boc, For, Fmoc or Ac. However, to obtain a peptide with the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly, the amino acid residue(s) W will need to be removed after the enzymatic coupling. For this purpose, an Edman-type protective group (P) is typically used in accordance with the invention (see also below). The inventors found that such group is also particularly suitable as a protective group for the N-terminal α-amine function of the peptide C-terminal (thio)ester during an enzymatic coupling reaction or a (further) functionalisation at a side-chain of the peptide that has been formed by the coupling reaction (such as the side chain of amino acid residue Y) according to the invention. The protective group P may be present during the enzymatic coupling (q=1). However, good results are also achieved in an enzymatic coupling wherein P is not present (q=0). Then, the Edman-type group P is introduced after the enzymatic coupling (before or after further functionalisation of Y, if any) and used to remove the amino acid residue(s) W.

Suitable protection conditions when using Edman-type moieties and suitable conditions to cleave P-W from the peptide include those that are generally known in the art for using such moiety in Edman-type degradation methods. Labelling of P to the N-terminal α-amino function of the peptide is accomplished in a manner known per se, based on the Edman type methodology known for said P, typically at mildly alkaline conditions, e.g. about pH 8. Cleavage of P-W from the N-terminal α-amino function of the peptide is accomplished in a manner known per se, based on the Edman type methodology known for said P, typically at acidic conditions, usually at a pH of about 4 or less, in particular in the range of about 3 or less, e.g. of 0-2. E.g. trifluoroacetic acid (TFA) may be used.

Suitable protective moieties that can be labelled to the N-terminal α-amino function of a peptide via a linking amino acid residue and cleaved off together with the linking amino acid residue are therefore also referred to herein as 'Edman-type protective groups'.

A substituted thiocarbamoyl group (P) has been found particularly effective as an Edman-type protective group, usually in combination with contributing to good solubility, also in an aqueous reaction medium. The substituted thiocarbamoyl group can be aromatic or aliphatic. Preferably the substituted thiocarbamoyl group is an aryl-substituted thiocarbamoyl group, or an alkyl-substituted thiocarbamoyl group. Particularly preferred aryl-substituted thiocarbamoyl groups are C6-C12-aryl-substituted thiocarbamoyl groups, more in particular phenylthiocarbamoyl (PTC). Particularly preferred alkyl-substituted thiocarbamoyl groups are C1-C6-alkyl-substituted thiocarbamoyl groups, more in particular methylthiocarbamoyl (MTC). Further examples of preferred isothiocyanates to be used for the introduction of substituted thiocarbamoyl groups are those mentioned in H. Matsunaga, T. Santa, K. Hagiwara, H. Homma, K. Imai, S. Uzu, K. Nakashima, S. Akiyama, Anal. Chem. 1995, 67, 4276, such as FITC, BAMPITC, DNTC, DNSAPITC, dansylamino-PITC, 3-POPICs, 4-POPICs, CIPIC and 7-[(N,N-dimethylamino)sulphonyl]-2,1,3-benzoxadiazol-4-yl isothiocyanate (DBD-NCS), see the paragraph bridging the left-hand and right hand column of page 4276, incorporated by reference. Yet another preferred example is 7-aminosulphonyl-4-(2,1,3-benzoxadiazolyl)-isothiocyanate (ABD-NCS).

Substituted thiocarbamoyl groups can be provided to the N-terminal α-amino function by reacting said amine function with the corresponding isothiocyanate under (slightly) alkaline conditions. Hence, a phenylthiocarbamoyl (PTC) group can be introduced using phenylisothiocyanate (PITC) and a methylthiocarbamoyl (MTC) group can be introduced using methylisothiocyanate (MITC). Under acidic conditions such substituted thiocarbamoyl groups are cleaved from the peptide together with the α-amino acid to which they are attached in the form of a thiazolinone derivative.

As an alternative to a substituted thiocarbamoyl moiety, another moiety suitable for sequencing amino acids in a peptide with an Edman-type degradation method can be used as a protective group in a similar fashion, i.e. by labelling the N-terminal α-amine function of the peptide C-terminal (thio)ester with said moiety via a linking amino acid and, after enzymatic coupling with the peptide nucleophile—cleaving the moiety together with the linking amino acid residue from the remainder of the coupling product.

This new way of providing N-terminal protection, using an Edman-type protective group has been found advantageous over, e.g., Fmoc with respect to solubility in an aqueous reaction system. It has been found advantageous over, e.g. Boc, in terms of compatibility when using solid-phase synthesis. An Edman-type protective group, such as a substituted thiocarbamoyl moiety, functions particularly well as a protective group at neutral or alkaline pH and can be easily removed at acidic pH. Thus, such group is usually employed in a coupling reaction at neutral or alkaline pH, using a ligase having a good S/H ratio at such pH, like a Subtilisin BPN' variant or homologue, as described in more detail elsewhere herein.

Further, it is possible to link an Edman-type protective group to the peptide C-terminal (thio)ester via more than one amino acid (i.e. via a peptide chain $W_v$, wherein v is >1). The linking amino acids can then be removed by a number of cycles of labeling with a moiety P and cleaving off the moiety plus amino acid, in a similar way as is done in a peptide sequencing method. The use of additional linking amino acids is not necessary, but they can be used—if desired—e.g. to modify the solubility of the peptide C-terminal (thio)ester in a reaction medium of choice.

As a general note: apart from the Edman-type protective groups P being useful to remove amino acid moieties W, N-terminal protection of the peptide (thio)ester with an Edman-type protective group is in particular useful in a method wherein Y comprises a Lys(γ-Glu-OH) moiety bearing a free α-amino function which needs to be coupled to a fatty acid, such as palmitic acid, or if Y comprises a Lys(AEEA-AEEA-γ-Glu-OH) moiety or the like bearing a free α-amino function which needs to be coupled to a fatty acid, such as 17-carboxy-heptadecanoic acid.

Further, it is observed that in particular good results have been achieved with a peptide C-terminal (thio)ester without protected side-chain functionalities. However, in an embodiment, a side-chain functionality, in particular the side chain of $^3$Glu of the peptide C-terminal (thio)ester, is provided with a protecting group. Suitable protecting groups are known to the person skilled in the art. Carboxylic acid groups can for instance be protected with a cyclohexyl, benzyl or allyl group.

The peptide C-terminal (thio)ester typically is an activated (thio)ester, i.e. it contains a carboxy ester or carboxy thioester group that can take part in the enzymatic coupling reaction. In principle, any (substituted or unsubstituted) alkyl or (substituted or unsubstituted) aryl (thio)ester can be used. Typical examples of (thio)esters which can take part in the enzymatic coupling reaction are methyl-, ethyl, propyl-, isopropyl-, phenyl-, benzyl- (such as p-carboxy-benzyl-), 2,2,2-trichloroethyl-, 2,2,2-trifluoroethyl-, cyanomethyl- and carboxyamidomethyl-(thio)esters.

Particularly good results have been obtained with carboxyamidomethyl-type esters (Cam-esters) represented by the formula peptide-(C=O)—O—$CX_1X_2$—C(=O)N—$R_1R_2$. Herein, each $X_1$ and $X_2$ independently represents a hydrogen atom or an alkyl group. Good results have been achieved when both $X_1$ and $X_2$ are a hydrogen atom (peptide-(C=O)—O—$CH_2$—C(=O)N—$R_1R_2$). Herein $R_1$ represents a hydrogen atom or an alkyl group and $R_2$ represents a hydrogen atom or an alkyl group or an amino acid or a peptide residue with a C-terminal carboxyamide or carboxylic acid functionality, optionally protected on the side-chain functionality of the amino acid or on one or more of the side-chain functionalities of the amino acids. Herein, each alkyl group may independently represent a (substituted or unsubstituted) C1-C7 alkyl group, preferably a (substituted or unsubstituted) linear C1-C6 alkyl group, more preferably a (substituted or unsubstituted) linear C1-C3 alkyl group, and most preferably a methyl group. Good results have in particular been achieved in a method of the invention wherein both $R_1$ and $R_2$ represent a hydrogen atom or wherein $R_1$ represents a hydrogen atom and $R_2$ represents an amino acid or peptide residue with a C-terminal carboxyamide or carboxylic acid functionality, optionally protected on the side-chain functionality of the amino acid or on one or more of the side-chain functionalities of the amino acids.

It is especially advantageous to use a Cam-AA1-AA2-ester, wherein AA1 is a first amino acid residue and AA2 is a second amino acid residue. Herein AA1 is a hydrophobic amino acid residue, such as an alanine, valine, leucine, isoleucine, phenylalanine, methionine or tryptophan unit. AA2 is a basic amino acid residue, such as an arginine or a lysine unit. Particularly preferred are Cam-Phe-Arg and Cam-Phe-Lys. The AA1 and the AA2 typically have a free side-chain functionality, i.e. that is free of a protective group or another residue.

Particularly good results have also been obtained with carboxyl substituted benzyl esters, in particular with p-carboxyl substituted benzyl esters represented by the formula peptide-(C=O)—O—$CH_2$—$C_6H_4$—$CO_2E$ wherein E represents a hydrogen atom, a positively charged salt ion such as an ammonium ion, or an amino acid or a peptide residue with a C-terminal carboxyamide or carboxylic acid functionality, optionally protected on the side-chain functionality of the amino acid or on one or more of the side-chain functionalities of the amino acids. Good results have also been obtained with p-carboxyl substituted benzyl esters represented by the formula peptide-(C=O)—O—$CH_2$—$C_6H_4$—$CO_2E$ wherein E is defined as above and in which one or more hydrogen atoms in the phenyl ring ($C_6H_4$ in the above formula) are replaced by a substituent, such as hydroxy, alkoxy, aryloxy or halogen.

The activated C-terminal (thio)ester group of the peptide C-terminal (thio)ester can be synthesized using solid phase synthesis in high yield and purity without racemization. An additional advantage of the use of (thio)esters of the carboxyamidomethyl type wherein $R_1$ represents a hydrogen atom and $R_2$ represents an amino acid or peptide residue with a C-terminal carboxylic acid functionality, optionally protected on the side-chain functionality of the amino acid or on one or more of the side-chain functionalities of the amino acids is, that their activated C-terminal ester or thioester group can be synthesized using the cheap and industrially available 2-chlorotritylchloride resin.

The activated C-terminal (thio)ester group of the peptide C-terminal (thio)ester can also be synthesized by solution phase synthesis or by fermentation, i.e. using a microorganism. As generally known in the art, fermentative processes include production of a compound, i.e. a peptide under aerobic or anaerobic conditions. A reliable method to obtain peptide (thio)esters using fermentation is via so-called intein expression (see for instance E. K. Lee, Journal of Chemical Technology and Biotechnology, 2010, 9, 11-18). Different intein expression system kits are commercially available (for instance the IMPACT™ kit). Other methods for the fermentative production of peptide (thio)esters are known in the art.

The peptide nucleophile having an N-terminally unprotected amine comprises the amino acid sequence H-Gly-Thr-Phe-Thr-Ser-Asp-Val-Ser-Ser-Tyr-Leu-Glu-Gly-Gln-AlaAla-Y-Glu-Phe-Ile-Ala-Trp-Leu-Val-Z-Gly-Arg-Gly. ('the second peptide fragment'). Particularly good results have been achieved with a peptide nucleophile, wherein this is the amino acid sequence of the peptide nucleophile. It is in particular an important advantage of the present invention that—also in an aqueous system—the enzymatic coupling works well without needing the C-terminal end to be extended with a peptide tag or another derivative to enhance solubility or reactivity of the peptide nucleophile.

In an embodiment, the peptide nucleophile is C-terminal protected. In another embodiment it is free of C-terminal protection.

In particular, good results have been achieved with peptide nucleophiles without protected side-chain functionalities.

In an embodiment, one or more side-chain functionalities (in particular one or more hydroxyl, carboxyl or amine groups) of the peptide nucleophile are provided with a protecting group. Suitable protecting groups are known to the person skilled in the art. Carboxylic acid groups can for instance be protected with a cyclohexyl, benzyl or allyl group; amine functionalities can for instance be protected with an allyloxycarbonyl group or a trifluoroacetyl group.

The peptide nucleophile may be synthesized using methods known in the art, such as solid-phase synthesis, solution phase synthesis or by fermentation.

As mentioned above, Y is Lys, whose Lys side-chain ε-amino group may be protected with a protective group. However, it is generally not necessary for a satisfactory coupling yield and rate to protect the side-chain ε-amino group, in particular not if a subtilisin or homologue thereof is used as the ligase. In particular, a subtilisin BPN' variant or homologue as described herein is suitable to couple both fragments also when the ε-amino group of Lys at position Y is free of a protective group.

Accordingly, usually the Y of the peptide nucleophile is a lysine residue having a free side chain ε-amino group or having a functionalised side chain ε-amino group.

The enzymatic coupling of the peptide C-terminal (thio)ester and the peptide nucleophile yields a peptide with at least one additional amino acid residue W and optionally a group P, i.e. it yields a coupling product comprising $P_q$-$W_v$-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly.

Thus, the coupling product can be represented by the formula (i):

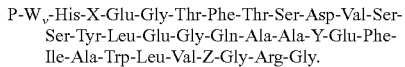
P-W$_v$-His-X-Glu-Gly-Thr-Phe-Thr-Ser-Asp-Val-Ser-
Ser-Tyr-Leu-Glu-Gly-Gln-Ala-Ala-Y-Glu-Phe-
Ile-Ala-Trp-Leu-Val-Z-Gly-Arg-Gly.

In order to obtain a peptide with the formula His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly, P-W is cleaved from the peptide with said formula (i), typically using Edman-type cleaving conditions suitable for said group P. This cleaving yields a peptide represented by the formula:

W$_{v-1}$-His-X-Glu-Gly-Thr-Phe-Thr-Ser-Asp-Val-Ser-
Ser-Tyr-Leu-Glu-Gly-Gln-Ala-Ala-Y-Glu-Phe-
Ile-Ala-Trp-Leu-Val-Z-Gly-Arg-Gly.

If v is larger than 1, a further W is removed by first coupling a group P to the N-terminal α-amine function of this peptide, thereby obtaining P-W$_{v-1}$-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly.
By cleaving P-W from said peptide a further peptide is obtained, represented by the formula:

W$_{v-2}$-His-X-Glu-Gly-Thr-Phe-Thr-Ser-Asp-Val-Ser-
Ser-Tyr-Leu-Glu-Gly-Gln-Ala-Ala-Y-Glu-Phe-
Ile-Ala-Trp-Leu-Val-Z-Gly-Arg-Gly.

The coupling of a P and subsequent cleaving of a P-W can then be repeated till the peptide of interest is obtained, typically a peptide having the sequence:

His-X-Glu-Gly-Thr-Phe-Thr-Ser-Asp-Val-Ser-Ser-
Tyr-Leu-Glu-Gly-Gln-Ala-Ala-Y-Glu-Phe-Ile-
Ala-Trp-Leu-Val-Z-Gly-Arg-Gly.

Alternatively, enzymatic coupling of the peptide C-terminal (thio)ester and the peptide nucleophile yields a peptide with at least one additional amino acid residue W yet without a P group (when q=0 for the peptide C-terminal ester or thioester). Such coupling product can be represented by formula (ii)

W$_v$-His-X-Glu-Gly-Thr-Phe-Thr-Ser-Asp-Val-Ser-
Ser-Tyr-Leu-Glu-Gly-Gln-Ala-Ala-Y-Glu-Phe-
Ile-Ala-Trp-Leu-Val-Z-Gly-Arg-Gly.

In case Y has a γ-Glu with a free α-amine function, this method is less suitable, because this amine function may participate in the enzymatic coupling reaction. However, this method works well, in other cases, e.g. when Y is Lys with a free ε-amine function (in which case pH is usually chosen such that the ε-amine function is protonated) or when Y is fully functionalised with a fatty acid, such as to obtain Semaglutide or Liraglutide. Any amino acid residue W can then be removed in an analogous manner as described for the coupling product represented by formula (i), i.e. by labelling the N-terminal W with an Edman-type protective group P, to yield the product represented by the formula P-W$_v$-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly and cleaving P-W to obtain a peptide represented by the formula W$_{v-1}$-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly. The coupling of a P and subsequent cleaving of a P-W can then be repeated till the peptide of interested is obtained, typically a peptide having the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly.
The coupling product obtained by the enzymatic coupling can be the peptide of interest (after removal of the protecting group(s)), e.g. if GLP-1 is the peptide of interest to be synthesised or if Y of the peptide nucleophile already comprises the needed functionalisation to obtain Liraglutide or Semaglutide. Alternatively, the product obtained by enzymatic coupling can subsequently be subjected to further reactions to functionalise it, in particular with an amino acid or another functional group, more in particular a functional group selected from the group consisting of Pal-γ-Glu-OH, and AEEA-AEEA-γ-Glu-N-17-carboxyheptadecanoyl-OH, wherein Pal is palmitoyl and AEEA-AEEA is 2-[2-(2-aminoethoxy)ethoxy]acetyl-2-[2-(2-aminoethoxy)ethoxy]acetyl. Ways to functionalise the free ε-amino side chain of Y to yield Liraglutide or Semaglutide or to provide the peptide nucleophile suitable for synthesising Liraglutide or Semaglutide can be based on methodology generally known in the art or may be based on the present examples or on the technology described in the literature referred to in the references cited herein. In particular, a functionalisation protocol may be used based on U.S. Pat. No. 6,451,974 B1.

In a preferred embodiment, the invention relates to a method for synthesising Semaglutide or a coupling product which yields Semaglutide upon removal of P$_q$-W$_v$, and—if still needed—functionalisation of Y. There are several particularly preferred possibilities to carry out the method to provide Semaglutide or a coupling product to prepare Semaglutide from.

A first particularly preferred embodiment to achieve this comprises the enzymatic coupling—catalysed by the ligase—of
(a) the peptide C-terminal ester or thioester comprising the sequence P$_q$-W$_v$-His-Aib-Glu-(thio)ester, and
b) the peptide nucleophile comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Arg-Gly-Arg-Gly, wherein Y is Lys(AEEA-AEEA-γ-Glu-N-17-carboxyheptadecanoyl-OH).
This method yields Semaglutide without needing post-enzymatic functionalisation of Y. The enzymatic coupling can be carried out with a high yield of the desired peptide with either P being present (q=1) or P being absent (q=0). If P is absent during enzymatic coupling, the coupling product can be labelled with an Edman-type protective group P, after which P-W can be cleaved from the coupling peptide. Thus, in practice an Edman-type protective group P is usually present during the enzymatic coupling in order to produce Semaglutide, because such group is needed to remove the amino acid residue(s) W$_v$.

A second particularly preferred method to provide Semaglutide or a coupling product to prepare Semaglutide from comprises the enzymatic coupling—catalysed by the ligase—of
(a) the peptide C-terminal ester or thioester comprising the sequence P-W$_v$-His-Aib-Glu-(thio)ester, and
(b) the peptide nucleophile comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Arg-Gly-Arg-Gly, wherein Y is Lys(AEEA-AEEA-γ-Glu-OH).

Thereby a peptide coupling product is formed comprising the formula P-W$_v$-His-Aib-Glu-Gly-Thr-Phe-Thr-Ser-Asp-Val-Ser-Ser-Tyr-Leu-Glu-Gly-Gln-Ala-Ala-Lys(AEEA-AEEA-γ-Glu-OH)-Glu-Phe-Ile-Ala-Trp-Leu-Val-Arg-Gly-Arg-Gly.

Next, the Lys(AEEA-AEEA-γ-Glu-OH) is provided with a 17-carboxyheptadecanoyl group to obtain P-W$_v$-His-Aib-Glu-Gly-Thr-Phe-Thr-Ser-Asp-Val-Ser-Ser-Tyr-Leu-Glu-Gy-Gn-Ala-Ala-Lys(AEEA-AEEA-γ-Glu-N-17-carboxyheptadecanoyl-OH)-Glu-Phe-Ille-Ala-Trp-Leu-Val-Arg- Gly-Arg-Gly. This can be done using reaction conditions known per se for the preparation of Semaglutide. P-$W_v$ is then removed after coupling of the fatty acid, using Edman-type methodology as described elsewhere herein, to obtain Semaglutide.

A third particularly preferred method to provide Semaglutide or a coupling product to prepare Semaglutide from, comprises the enzymatic coupling—catalysed by the ligase—of
(a) the peptide C-terminal ester or thioester comprising the sequence $P_q$-$W_v$-His-Aib-Glu-(thio)ester, and
(b) the peptide nucleophile comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Arg-Gly-Arg-Gly, wherein Y is a lysine residue having a free or protected ε-amino side chain, and thereafter providing the ε-amino side chain of the Lys with a AEEA-AEEA-γ-Glu-N-17-carboxyheptadecanoyl-OH group.

The enzymatic coupling and providing the Lys ε-amine function with an AEEA-AEEA-γ-Glu-N-17-carboxyheptadecanoyl-OH group are achieved with high yield also in the absence of the P group. The P group can already be present during enzymatic coupling and/or functionalization, but is generally only needed to remove the amino acid residue(s) W. One may remove the amino acid residue(s) W after enzymatic coupling yet before functionalization of the Lys ε-amine function. However, it is practical to first provide the Glu-fatty acid block and then cleave off W, using an Edman-type protective group (P).

Further, good results have been achieved in accordance with the invention in the synthesis of Liraglutide respectively a coupling product from which Liraglutide can be prepared upon removal of $P_q$-$W_v$.

In a first advantageous embodiment, the preparation of Liraglutide (or the coupling product from which Liraglutide can be prepared) comprises the enzymatic coupling, catalyzed by the ligase, of
(a) the peptide C-terminal ester or thioester comprising the sequence $P_q$-$W_v$-His-Ala-Glu-(thio)ester, and
(b) the peptide nucleophile comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Arg-Gly-Arg-Gly, wherein Y is Lys(Pal-γ-Glu-OH).

Herein, good results have also been achieved with q=0 during the enzymatic coupling. A group P can be present during enzymatic coupling though. If q=0 during the enzymatic coupling, an Edman-type group P is provided to the N-terminal α-amino function after enzymatic coupling to remove any amino acid residue W in order to obtain Liraglutide. For practical reasons, such group P is usually present during the enzymatic coupling though.

In a second advantageous embodiment, the preparation of Liraglutide (or the coupling product from which Liraglutide can be prepared) comprises the enzymatic coupling, catalyzed by the ligase, of
(a) the peptide C-terminal ester or thioester comprising the sequence P-$W_v$-His-Ala-Glu(thio)ester, and
(b) the peptide nucleophile comprising the sequence H-Gly-Thr-Phe-Thr-Ser-Asp-Val-Ser-Ser-Tyr-Leu-Glu-Gly-Gln-Ala-Ala-Lys(γ-Glu-OH)-Glu-Phe-Ile-Ala-Trp-Leu-Val-Arg-Gly-Arg-Gly;
thereby obtaining a peptide represented by the formula P-$W_v$-His-Ala-Glu-Gly-Thr-Phe-Thr-Ser-Asp-Val-Ser-Ser-Tyr-Leu-Glu-Gly-Gln-Ala-Ala-Lys(γ-Glu-OH)-Glu-Phe-Ile-Ala-Trp-Leu-Val-Arg-Gly-Arg-Gly, and thereafter
providing said Lys(γ-Glu-OH) of said peptide with a palmitoyl group (Pal), to obtain P-$W_v$-His-Ala-Glu-Gly-Thr-Phe-Thr-Ser-Asp-Val-Ser-Ser-Tyr-Leu-Glu-Gly-Gln-Ala-Ala-Lys(Pal-γ-Glu)-Glu-Phe-Ile-Ala-Trp-Leu-Val-Arg-Gly-Arg-Gly. P-$W_v$ is then removed using Edman-type methodology as described elsewhere herein, to obtain liraglutide.

In a third advantageous embodiment, the preparation of Liraglutide (or the coupling product from which Liraglutide can be prepared) comprises the enzymatic coupling, catalyzed by the ligase, of
(a) the peptide C-terminal ester or thioester comprising the sequence $P_q$-$W_v$-His-Ala-Glu-(thio)ester, and
(b) the peptide nucleophile comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Arg-Gly-Arg-Gly, wherein Y is a lysine residue having a free or protected ε-amino side chain; and thereafter providing said ε-amino side chain with Pal-γ-Glu-OH. $P_q$-$W_v$ can be removed based on the methodology described herein above.

Further, a method according to the invention is particularly suitable to prepare GLP-1. Such method generally comprises the enzymatic coupling of $P_q$-$W_v$-His-Ala-Glu-(thio)ester with Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly. $P_q$-$W_v$ can be removed based on the methodology described herein above.

The ligase used to catalyse the coupling of the peptide C-terminal (thio)ester and the peptide nucleophile can be any ligase having catalytic activity in coupling both peptides by catalysing the formation of a peptide bond between the C-terminus of the peptide C-terminal (thio)ester and the N-terminus of the peptide nucleophile, wherein the S/H ratio for the coupling vs. the hydrolysis of the coupling product in the used reaction medium is larger than 1. Usually, the ligase can be classified as a serine protease which can generally be classified in EC 3.4.21. Generally, it has a catalytic triad in the order Asp, His and Ser.

In particular, a ligase used in a method according to the invention is an isolated enzyme. Thus, it is isolated from the organism wherein it has been expressed, typically a recombinant organism, if it has been produced in an organism, respectively isolated from the reaction medium in which it has been synthesized.

In particular, an enzyme of the invention is considered isolated for the purpose of the invention either in the crude form or substantially purified by any suitable technique such as, for example, the single-step purification method disclosed in Smith and Johnson, Gene 67:31-40 (1988).

In particular, the ligase can be a serine endoprotease. The ligase typically has an S/H ratio larger than 1, preferably 2 or more, in particular 5 or more in the used reaction medium, in particular in a reaction medium comprising water, more in particular an aqueous medium. The upper value of this quotient is not critical; in practice it may e.g. be 100 or less, in particular 20 or less. The ligase used in a method according to the invention generally has an improved "synthesis over hydrolysis ratio" (S/H ratio), at least compared to subtilisin BPN'.

The S/H ratio of the ligases (used in a method) according to the invention divided by the S/H ratio of subtilisin BPN'—at least under the conditions described in the examples—is usually more than 100, preferably 250 or more, more preferably 500 or more, in particular 1000 or more. The upper value of this quotient is not critical; it may approximate infinity.

In particular, very good results have been achieved with a subtilisin BPN' variant or a homologue thereof.

Especially when carrying out the enzymatic coupling in a reaction medium comprising water as a major solvent (e.g. 50-100 wt. % based on total liquid) a subtilisin BPN' variant or a homologue thereof according to WO 2016/056913 has been found particularly suitable. The contents of the publication are incorporated by reference, in particular with respect to the details about the subtilisin BPN' variant or a homologue, as present in the claims thereof. Thus, usually, the ligase used for the coupling reaction is a subtilisin BPN' variant or a homologue thereof comprising the following mutations compared to subtilisin BPN' represented by SEQUENCE ID NO: 2 or a homologue sequence thereof:

a deletion of the amino acids corresponding to positions 75-83;

a mutation at the amino acid position corresponding to S221, the mutation being S221C or S221 selenocysteine;

preferably a mutation at the amino acid position corresponding to P225;

wherein the amino acid positions are defined according to the sequence of subtilisin BPN' represented by SEQUENCE ID NO: 2.

Further preferred ligases for use in a method according to the invention may comprise one or more additional mutations, in particular one or more further mutations as identified elsewhere herein or in WO 2016/056913, incorporated herein by reference.

The mutation at the amino acid position corresponding to S221 of the ligase, in particular the subtilisin BPN' variant or homologue thereof, preferably is S221C.

The mutation at the amino acid position corresponding to P225 is usually advantageous for the S/H ratio for the enzymatic coupling. The mutation is usually selected from the group of P225N, P225D, P225S, P225C, P225G, P225A, P225T, P225V, P225I, P225L, P225H, P225Q, preferably from the group of P225N, P225D, P225S, P225C and P225G, more preferably P225N or P225D, most preferably P225N.

For a good enzyme stability, the ligase, in particular the subtilisin BPN' variant or homologue thereof, preferably comprises one or more mutations selected from the group of mutations at an amino acid position corresponding to Q2, S3, P5, S9, I31, K43, M50, A73, S188, Q206, N212, N218, T254 and Q271 of SEQUENCE ID NO 2.

A preferred mutation at the position corresponding to Q2 corresponds to Q2K.

A preferred mutation at the position corresponding to S3 corresponds to S3C.

A preferred mutation at the position corresponding to P5 corresponds to P5S.

A preferred mutation at the position corresponding to S9 corresponds to S9A.

A preferred mutation at the position corresponding to I31 corresponds to I31L.

A preferred mutation at the position corresponding to K43 corresponds to K43N.

A preferred mutation at the position corresponding to M50 corresponds to M50F.

A preferred mutation at the position corresponding to A73 corresponds to A73L.

A preferred mutation at the position corresponding to A188 corresponds to S188P.

A preferred mutation at the position corresponding to Q206 corresponds to Q206C.

A preferred mutation at the position corresponding to N212 corresponds to N212G.

A preferred mutation at the position corresponding to T254 corresponds to T254A.

A preferred mutation at the position corresponding to Q271 corresponds to Q271E.

In a particularly preferred embodiment, the ligase, in particular the subtilisin BPN' variant or homologue thereof, comprises at least six, preferably at least eight, more preferably at least 10, in particular 12, 13 or 14 of said mutations selected from the group of mutations at positions corresponding to Q2, S3, P5, S9, I31, K43, M50, A73, S188, Q206, N212, T254 and Q271. This is in particular preferred for enzyme stability in a reaction medium comprising water as a major or the only solvent. The ligase may have further mutations compared to subtilisin BPN', provided that it has enzymatic fragment condensation activity (coupling activity) in the preparation of the peptides according to the present invention, in particular one or more further mutations as described in the references cited herein.

Alternatives to subtilisin BPN', as template enzymes from which an enzyme according to the invention, in particular a homologue of a subtilisin BPN' variant of the invention, can be derived by mutagenesis are other subtilisins, in particular subtilisins having at least 50% homology with subtilisin BPN'.

Sequences of suitable subtilisins can be retrieved from the UNIPROT sequence database (http://www.uniprot.org/), as available on 11 Aug. 2014, by BLASTing the database with subtilisin BPN' (SEQ ID 2) as a query. However, sequence retrieval is not limited to UNIPROT nor to the date. The skilled person in the art knows how to query alternative sequence depositories or to collect additional homologue sequences by sequencing (see for example *Zooming in on metagenomics: molecular microdiversity of Subtilisin Carlsberg in soil*. Gabor E, Niehaus F, Aehle W, Eck J. J Mol Biol. 2012 Apr. 20; 418(1-2):16-20). In particular, the invention further relates to variants, having at least said deletions of the amino acids corresponding to L75 till and including G83 of subtilisin BPN', cysteine or selenocystein at a position corresponding to position 221 in subtilisin BPN' and at least one of said further mutations in present claim 1.

The sequence of subtilisin BPN' is given in SEQUENCE ID NO: 2 (mature form). The gene encoding for subtilisin BPN' amino acids −107 to 275 is given in SEQUENCE ID NO: 1. The subtilisin BPN' variant or homologue can be based on the enzymes according to WO 2016/056913, with the proviso that it has the above-mentioned mutations.

In an advantageous embodiment, the ligase is a subtilisin BPN' variant having a deletion of the amino acids corresponding to positions 75-83, the mutation S221C and one or more further mutations, preferably at least 3 further mutations, in particular 5-8 further mutations, at amino acid positions corresponding to M222, Y217, P225, F189, N218, E156, G166 and N62 of wild-type subtilisin BPN' (mature). Of these mutations, in particular good results have been achieved with the mutations corresponding to: M222P, Y217H, P225N, F189W, N218D, E156N, G166E, N62A. SEQUENCE ID NO: 3 shows a subtilisin BPN' variant (for use) according to the invention with deletion of the $Ca^{2+}$ binding loop, S221C and having said further mutations. The His tag was included for facilitating purification and is not needed for ligase activity. Further preferred enzymes may comprise one or more additional mutations, in particular one or more further mutations as identified elsewhere herein or in WO 2016/056913, incorporated herein by reference.

In a particularly advantageous embodiment, the ligase is a subtilisin BPN' variant with SEQ ID NO 3, comprising the mutations Q2K, S3C, P5S, S9A, I31L, K43N, M50F, N62A, A73L, Δ75-83, E156N, G166E, G169A, S188P, F189W, Q206C, N212G, Y217H, N218D, S221C, M222P, P225N, T254A, Q271E, or a homologue thereof having at least 80%, or 85%, or 90%, preferably 95%, sequence identity, optionally comprising a His tag.

In a method of the invention the enzymatic reaction is typically performed in a fluid comprising water. Preferably the reaction is performed in a buffered fluid. The water content usually is 10-100 vol %, based on total liquids, preferably 20 vol. % or more, preferably 40 vol. % or more, in particular 50 vol. % or more, more in particular 60 vol. % or more. In particular good results have been achieved in a reaction medium, comprising 70-100 vol % water, more in particular 90-100 vol. %, 95-100 vol. % or 98-100 vol. % water. The term 'aqueous' is used for media at least substantially consisting of water.

In principle, any buffer is suitable. Good buffers are known to a person skilled in the art. See for instance David Sheehan in Physical Biochemistry, $2^{nd}$ Ed. Wiley-VCH Verlag GmbH, Weinheim 2009; http://www.sigmaaldrich-.com/ife-science/core-bioreagents/biological-buffers/learning-center/buffer-calculator.html. Particularly good results have e.g. been achieved with a Good's buffer, such as tricine. The concentration of the buffer may be chosen within wide limits, e.g. in the range of 10-1000 mM, in particular in the range of 25-500 mM, more in particular in the range of 50-250 mM. A relatively low molarity of the buffer has been found advantageous for coupling a peptide nucleophile wherein Y is Lys(Pal-γ-Glu-OH) or the like.

The pH of the buffer for a coupling reaction in a method according to the invention may be at least 5, in particular at least 6, preferably at least 7. A desired pH is usually less than 11, in particular less than 10, even more preferably less than 9. Usually the optimal pH for the enzymatic coupling is between 7 and 9.

Due to the high S/H ratio, a large excess of the peptide C-terminal ester or thioester or of the peptide nucleophile is generally not needed to reach a high yield in the condensation reaction. Generally, they are contacted in an about stoichiometric ratio or in an excess of the peptide C-terminal ester, in particular in a molar ratio of (a) the peptide C-terminal ester or thioester to (b) the peptide nucleophile in the range of 1:1 to 5:1. Although satisfactory results are achieved with a stoichiometric ratio, an excess of the peptide C-terminal (thio)ester has been found advantageous for the reaction rate. Thus, preferably the molar ratio of (a) the peptide C-terminal ester or thioester to (b) the peptide nucleophile is in the range of 1.05:1.0 to 4:1, more preferably in the range of 1.1:1.0 to 3:1, even more preferably in the range of 1.2:1.0 to 2.5:1.0, in particular in the range of 1.2:1.0 to 2.0:1.0.

In a method of the invention, it may be advantageous to add additives to the fluid wherein the reaction is carried out to improve the solubility of the peptide fragments or to improve the reaction yield. Such additives may be a salt or an organic molecule, for instance guanidinium hydrochloride, urea, sodium dodecasulphate or Tween. However, good results have been achieved without such additive, also in an fully aqueous reaction medium, e.g. in an embodiment wherein the Y is Lys(Pal-γ-Glu-OH) or the like.

The reaction may be carried out in a fully aqueous liquid or in a mixture of water and a water miscible co-solvent such as N,N-dimethylformamide (DMF), N-methyl-pyrrolidinone (NMP), N,N-dimethylacetamide (DMA), dimethylsulphoxide (DMSO), acetonitrile, an ether, such as tetrahydrofuran (THF), 2-methyl-tetrahydrofuran (Me-THF) or 1,2-dimethoxyethane, or a (halogenated) alcohol, such as methanol, ethanol, isopropanol, tert-butanol, 2,2,2-trifluoroethanol (TFE), 1,1,1,3,3,3-hexafluoroisopropanol, or a mixture of these organic solvents. Depending on the stability of the subtilisin BPN' variant and the solubility of the peptide substrates, the amount of co-solvent is preferably below 70 vol %, more preferably below 60 vol %, even more preferably below 50 vol %, and most preferably below 40%.

In principle the temperature during the enzymatic fragment condensation is not critical, as long as a temperature is chosen at which the ligase to be used shows sufficient activity and stability. Such a temperature can be routinely determined. Generally, the temperature may be at least −10° C., in particular at least 0° C. or at least 10° C. Generally, the temperature may be 70° C. or less, in particular 60° C. or less or 50° C. or less. Optimal temperature conditions can easily be identified for a specific ligase for a specific enzymatic fragment condensation by a person skilled in the art through routine experimentation based on common general knowledge and the information disclosed herein. In general, the temperature advantageously is in the range of 20-50° C.

The invention further relates to the use of an Edman-type agent to provide a protective group in the synthesis of a peptide in a method comprising enzymatic coupling of peptides by fragment condensation. Accordingly, the invention further relates to a method for synthesizing a peptide, comprising enzymatically coupling (a) a peptide C-terminal ester or thioester represented by the formula P-$W_v$-$AA_n$-(thio)ester with (b) a peptide nucleophile represented by the formula $AA_m$, which coupling is catalysed by a ligase, preferably a subtilisin BPN' variant or homologue, such as described elsewhere herein.

Herein P represents the Edman-type protective group, as defined above, preferably a thiocarbamoyl group. Coupling of P to the N-terminal end of the peptide is accomplished in a manner known per se, based on the Edman type methodology known for said P, typically at mildly alkaline conditions, e.g. about pH 8. Herein v is an integer of at least 1, usually preferably 1-10, preferably 1-5, more preferably 1, 2 or 3, most preferably 1 and v representing the number of amino acid residues W, wherein each W can be the same or different, and preferably is as defined as above. Each AA stands for an amino acid residue, n is an integer representing the number of amino acid residues of the peptide C-terminal ester or thioester, and m is an integer representing the number of amino acid residues of the peptide nucleophile. Typically, the sum of n and v is at least 4 in order to allow recognition by the ligase. Preferably, n is in the range of 3-200, in particular in the range of 3-50, more in particular in the range of 3-25. In a specific embodiment, n is at least 4, at least 6, at least 8, at least 10, at least 15 or at least 20. Preferably, m is in the range of 3-200, in particular in the range of 5-50, more in particular in the range of 8-30. In a specific embodiment, m is at least 4, at least 10, at least 15 or at least 20.

The coupling product, P-$W_v$-$AA_n$-$AA_m$ is subject to a cleavage reaction wherein the peptide $W_{v-1}$-$AA_n$-$AA_m$ is formed. Typically, cleavage is accomplished under acidic conditions. If v-1>0, thereafter a group P is coupled to the W at the N-terminal position of the peptide $W_{v-1}$-$AA_n$-$AA_m$, to form P-$W_{v-1}$-$AA_n$-$AA_m$ after which P-W is cleaved. This is then repeated till the peptide represented by formula $AA_n$-$AA_m$ is obtained.

The invention will now be illustrated by the following examples, without being limited thereto.

EXAMPLES

Production of Ligases
Mutagenesis, Cloning and Expression
Sequence ID NO: 1 shows the wild type gene coding for subtilisin BPN' amino acids −107 to 275. Herein the codons coding for amino acids −107 to −1 are present. These amino acids comprise the signal sequence, the pre-sequence and a pro-sequence which are cleaved off upon full maturation. Sequence ID NO: 2 shows the mature wild type subtilisin BPN' (i.e. without the amino acids −107 to −1). The ligase used for the Examples was as shown in Sequence ID NO: 3. Compared to the mature wild type subtilisin BPN', this ligase had the mutations Q2K, S3C, P5S, S9A, I31L, K43N, M50F, N62A, A73L, Δ75-83, E156N, G166E, G169A, S188P, F189W, Q206C, N212G, Y217H, N218D, S221C, M222P, P225N, T254A, and Q271E. Further, in order to facilitate a fast and efficient purification after amino acid 275 a C-terminal His-tag is attached as shown in SEQUENCE ID NO 3. The corresponding amino acid sequence is numbered according to the subtilisin BPN' numbering scheme. Thus, in order to maintain the subtilisin BPN' numbering for used ligases the numbering jumps from 74 to 83.

The gene coding for the ligase used for the following synthesis examples was obtained from GenScript. The genes were cloned (by GenScript) into a pUB-110 *E. coli-B. subtilis* shuttle vector (pBES) using the MluI and BamHI site based vector. In the shuttle vector, the expression of the gene is under the control of the aprE promoter. The vector contained the pUB ori of replication for *Bacillus* and a kanamycin resistance marker. The vector also contained the ColE1 ori of replication and an ampicillin resistance marker for maintenance in *E. coli*. The resulting plasmid pBES-ligaseHIS was propagated in *E. coli* TOP10 and transformed into *B. subtilis* GX4935 (trpC2 metB10 lys-3 ΔnprE ΔaprE).

Production and Purification of the Ligases

A single microbial colony of *B. subtilis* containing a plasmid with the subtilisin variant gene of interest was inoculated in 5 mL LB with kanamycin (10 µg/mL) at 37° C. in a shaking incubator. To the 30 mL Terrific Broth supplemented with antibiotic (kanamycin 10 µg/mL) and amino acids (100 mg/L Trp, 100 mg/L Met and 100 mg/L Lys) 0.6 mL of the overnight culture was added. The cells were grown for 48 h at 37° C. in a shaking incubator (200 rpm). The cells were harvested by centrifugation (15 min, 4,000 rpm, 4° C.). The medium (30 mL) was decanted and concentrated on an Sartorius Vivaspin 15R unit (15 mL, 10 kDa MW cut-off) in two centrifugation steps (15 min, 4000 rpm, 4° C.). The concentrated medium (0.5 mL) was then exchanged for buffer A (25 mM Tricine, pH 7.5, 0.5 M NaCl) in three washing/concentrating steps (14 mL buffer A, 10 min, 4,000 rpm, 4° C.). For His-tag purification Talon resin (2.5 mL, Clonetech) was added to a plastic column cartridge. The resin was washed with 20 mL MilliQ water and equilibrated with 20 mL of buffer A. The crude enzyme was loaded on the column and washed with 5 mL buffer A. The enzyme was eluted with 15 mL buffer B (25 mM Tricine, pH 7.5, 0.5 M NaCl, 500 mM imidazole). The elute was concentrated on Sartorius Vivaspin 15R (15 mL, 10 kDa MW cut-off) by centrifugation (15 min, 4000 rpm, 4° C.) and the buffer was exchanged to 25 mM Tricine, pH 7.5 in three washing/concentrating steps (15 mL buffer, 10 min, 4,000 rpm, 4° C.).

The purity of the protein was analyzed by SDS-PAGE and the enzyme concentration was determined as described in WO2016056913 (A1). The purity was more than 90%. The obtained aqueous solution (25 mM Tricine, pH 7.5) containing about 2 mg/mL of the obtained enzyme was used as such for the oligopeptide fragment condensations.

Enzymatic Fragment Condensation Examples

Materials and Methods

Unless stated otherwise, chemicals were obtained from commercial sources and used without further purification. In all enzymatic fragment condensations the ligase of SEQ ID:3 was used. Analytical HPLC was performed on an Agilent 1260 infinity Liquid Chromatograph, using a reversed-phase column (Phenomenex, C18, 5 µm particle size, 250×4.6 mm) at 40° C. UV detection was performed at 220 nm using a UV-VIS 204 Linear spectrometer. The gradient program was: 0-25 min linear gradient ramp from 5% to 98% eluent B and from 25.1-30 min 5% eluent B (eluent A: 0.5 mL/L methane sulfonic acid (MSA) in $H_2O$, eluent B 0.5 mL/L MSA in acetonitrile). The flow was 1 mL/min from 0-25.1 min and 2 mL/min from 25.2-29.8 min, then back to 1 mL/min until stop at 30 min. Injection volumes were 10 µL. Preparative HPLC was performed on a Varian PrepStar system using a stationary-phase column (Phenomenex, C18, 10 µm particle size, 250×50 mm). LC-MS was performed on an Agilent 1200 series Liquid Chromatograph, using a reversed-phase column (Phenomenex, C18, 5 µm particle size, 150×4.6 mm) at 40° C. UV detection and gradient program were as described for analytical HPLC. The molecular weights were determined using an Agilent 6130 quadrupole LC/MS system.

Protocol 1: Synthesis of Fmoc-Glycolic Acid

Tert-butyl 2-hydroxy-acetate (2.5 g) was dissolved in a mixture of pyridine (15 ml) and dichloromethane (DCM, 30 ml). Then Fmoc-chloride (5 g) in dry DCM (15 ml) was added dropwise at 0° C. The reaction mixture was stirred at room temperature for 24 hours. The solvent was removed under vacuum and the residue was redissolved in DCM (40 ml), washed with 1M sodium bicarbonate solution (20 mL) twice, brine solution (20 ml) twice, dried over anhydrous magnesium sulfate and concentrated. The obtained Fmoc-glycolic acid tert-butyl ester (4 g) was dissolved in trifluoroacetic acid (TFA), triisopropylsilane (TIS) and water (95/2.5/2.5, v/v/v, 15 mL) and stirred for 120 min. The solvent was removed under vacuum and the viscous residue was redissolved in 5% sodium bicarbonate solution (150 ml), washed with diethyl ether (75 ml) 3 times. The aqueous solution was then mixed with ethyl acetate (45 mL) and acidified with 40% phosphoric acid to pH=2 at 0° C. The organic layer was collected and dried with anhydrous magnesium sulfate. The solvent was removed under vacuum to give the final product Fmoc-glycolic acid (Fmoc-GA).

Protocol 2: Synthesis of Oligopeptide-OCam-Leu-OH Esters 1 gram of preloaded Fmoc-Leu-Wang resin (with a loading of 0.81 mmol/gram) was washed with DCM (2×2 min, 10 mL) and N,N'-dimethylformamide (DMF, 2×2 min, 10 mL) and Fmoc-deprotected using piperidine/DMF (1/5, v/v, 2×8 min, 10 mL). After washing with DMF (6×2 min, 10 mL), Fmoc-GA (4 equiv.) was coupled to the resin using 2-(1H-benzotriazol-1-yl)-1,1,3,3-tetramethyluronium hexafluorophosphate (HBTU, 4 equiv.), OxymaPure (4 equiv.) and di-isopropylethylamine (DIPEA, 8 equiv.) in DMF (45 min, 10 mL). After washing with DMF (2×2 min, 10 mL) the resin was Fmoc-deprotected using piperidine/DMF (1/5, v/v, 2×8 min, 10 mL). The Cam-Leu-OH ester was formed by coupling of the first Fmoc-protected amino acid using 4 equiv. Fmoc-Xxx-OH, 4 equiv. N,N'-diisopropylcarbodiimide (DIC) and 0.1 equiv. 4-dimethylaminopyridine (DMAP) in DMF (2×60 min, 10 mL). Here and in other parts of this disclosure 'Xxx' stands for one amino acid (variable as indicated in the sequences in the examples below). For the Semaglutide starting material a commercially available Fmoc-Aib-OH building block was used.

After washing with DMF (6×2 min, 10 mL), standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using methyl tert-butyl ether (MTBE)ln-heptanes (1/1, v/v, 50 mL). The precipitated peptide was collected by centrifugation and washed twice with MTBEln-heptanes (1/1, v/v, 50 mL) followed by lyophilization from acetonitrile/water (1/1, v/v, 50 mL). The crude products were purified by preparative HPLC followed by lyophilization of the pure fractions.

Protocol 3: Synthesis of Oligopeptide C-Terminal Acid Nucleophiles 1 gram of preloaded Fmoc-Gly-Wang resin (with a loading of 0.30 mmol/gram) was washed with DCM (2×2 min, 10 mL) and DMF (2×2 min, 10 mL) and Fmoc-deprotected using piperidine/DMF (1/5, v/v, 2×8 min, 10 mL). Standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using MTBEln-heptanes (1/1, v/v, 50 mL). The precipitated peptide was collected by centrifugation and washed twice with MTBEln-heptanes (1/1, v/v, 50 mL) followed by lyophilization from acetonitrile/water (1/1, v/v, 50 mL). The crude products were purified by preparative HPLC followed by lyophilization of the pure fractions.

Protocol 4: PTC (Phenylthiocarbamoyl) Protection of H-Xxx-$^1$His-$^2$Ala-$^3$Glu-OCam-Leu-OH and H-Xxx-$^1$His-$^2$Aib-$^3$Glu-OCam-Leu-OH 100 mg of H-Xxx-$^1$His-$^2$Ala-$^3$Glu-OCam-Leu-OH or 100 mg of H-Xxx-$^1$His-$^2$Aib-$^3$Glu-OCam-Leu-OH was dissolved in 10 mL pyridine/water (1/1, v/v). To this mixture 25 mg of phenylisothiocyanate (PITC) was added and the solution was stirred at ambient temperature for 14 hours. The crude reaction mixture was diluted with 50 mL water and washed three times with 50 mL DCM. The water layer was purified by preparative HPLC followed by lyophilization of the pure fractions.

Instead of phenylisothiocyanate, giving the phenylthiocarbamoyl (PTC) protected peptide, other Edman reagents could be used, such as methylisothiocyanate (MITC), giving the methylthiocarbamoyl (MTC) protected peptide.

Protocol 5: Synthesis of Pal-γ-Glu Containing Peptides

General protocol 3 was followed using commercially available Fmoc-Lys(Pal-γ-Glu-O$^t$Bu)-OH building blocks.

Protocol 6: Synthesis of the Semaglutide fragment H-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(AEEA-AEEA-γ-Glu-N-17-carboxyheptadecanoyl-OH)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH General protocol 3 was followed using a commercially available Fmoc-$^{20}$Lys(Mtt)-OH and Boc-$^4$Gly-OH building block. After SPPS of the Boc-4-31-Wang fragment the Mtt protecting group was removed using 10 mL of TIS/TFA/DCM (1/1/48, v/v/v, 3×15 min). Standard SPPS procedures were used for the coupling of Fmoc-AEEA-OH (twice), Fmoc-Glu-O$^t$Bu, and 17-carboxyheptadecanoyl-O$^t$Bu. Cleavage from the resin and side-chain deprotection was performed using a mixture of TFA/TIS/water (95/2.5/2.5, v/v/v, 15 mL) for 120 min. The crude peptide was precipitated using MTBEln-heptane (1/1, v/v, 50 mL). The precipitated peptide was collected by centrifugation and washed twice with MTBEln-heptane (1/1, v/v, 50 mL) followed by lyophilization from acetonitrile/water (1/1, v/v, 50 mL). The crude products were purified by preparative HPLC followed by lyophilization of the pure fractions.

Example 1

Enzymatic Synthesis of the Liraglutide Precursor PTC-Xxx-Liraglutide-1-31-OH Using a 3-Mer+28-Mer Approach.

In an HPLC vial, 10 mg of PTC-Phe-$^1$His-$^2$Ala-$^3$Glu-OCam-Leu-OH (i.e. the 3-mer providing amino acid residues 1-3 of Liraglutide) and 10 mg of H-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (i.e. the 28-mer providing amino acid residues 4-31 of Liraglutide) were dissolved in 475 µL water. To this mixture, 25 µL 1M tricine buffer pH 9.0 was added and the pH was adjusted to 8.7 using a 3M NaOH solution. Subsequently, 10 µL of TCEP (tris(2-carboxyethyl)phosphine) solution (100 mg/mL in water) and 10 µL of the ligase solution (10 mg/mL) were added. The mixture was left to react at ambient temperature. Every 15 minutes, 10 µL of the reaction mixture was withdrawn and quenched in 980 µL 5 vol % MSA in acetonitrile/water (2/1, v/v) and analysed using LC-MS.

After 90 minutes all Cam-ester starting material had been consumed, and the product and amine 28-mer starting material peaks were integrated. The ligation product PTC-Phe-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH was 82 area % and the leftover H-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH starting material was 18 area %.

The product PTC-Phe-Liraglutide-1-31-OH was obtained by preparative HPLC followed by lyophilization of the pure fractions.

Following the reaction as described above, almost identical results were obtained using PTC-Xxx-$^1$His-$^2$Ala-$^3$Glu-OCam-Leu-OH, wherein Xxx=Tyr, Leu, or Val or using MTC-Phe-$^1$His-$^2$Ala-$^3$Glu-OCam-Leu-OH.

Example 2

Enzymatic Synthesis of the Semaglutide Precursor PTC-Phe-Semaglutide-1-31-OH Using a 3-Mer+28-Mer Approach.

In an HPLC vial, 10 mg of PTC-Phe-$^1$His-$^2$Aib-$^3$Glu-OCam-Leu-OH (i.e. the 3-mer providing amino acid residues 1-3 of Semaglutide) and 10 mg of H-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (i.e. the 28-mer providing amino acid residues 4-31 of Semaglutide) were dissolved in 475 µL water. To this mixture, 25 µL 1M tricine buffer pH 9.0 was added and the pH was adjusted to 8.7 using a 3M NaOH solution. Subsequently, 10 µL of TCEP (tris(2-carboxyethyl)phosphine) solution (100 mg/mL in water) and 10 µL of the ligase solution (10 mg/mL) were added. The mixture was left to react at ambient temperature. Every 15 minutes, 10 µL of the reaction mixture was withdrawn and quenched in 980 µL 5 vol % MSA in acetonitrile/water (2/1, v/v) and analysed using LC-MS.

After 90 minutes all Cam-ester starting material had been consumed, and the product and amine 27-mer starting material peaks were integrated. The ligation product PTC-Phe- $^1$His-$^2$Aib-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH was 80 area % and the leftover H-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH starting material was 20 area %.

The product PTC-Phe-Semaglutide-1-31-OH was obtained by preparative HPLC followed by lyophilization of the pure fractions.

Example 3

Synthesis of H-Liraglutide-1-31-[$^{20}$Lys(Pal-γ-Glu)]-OH Using the PTC-Phe-Liraglutide-1-31-OH Precursor from Example 1 and Synthesis of H-Semaglutide-1-31-[$^{20}$Lys(AEEA-AEEA-γ-Glu-N-17-Carboxyheptadecanoyl-OH)]—OH Using the PTC-Phe-Semaglutide-1-31-OH Precursor from Example 2

2 mg of PTC-Phe-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH was dissolved in 500 μL water and 500 μL pyridine. To this solution, 2 mg of Pal-Glu-γ-hydroxy succinimide ester (Pal-Glu-OSu) was added and the mixture was left to react at ambient temperature for 5 hours followed by evaporation of the solvents in vacuo. The crude product PTC-Phe-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Pal-γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH was dissolved in 5 vol % trifluoroacetic acid in water for cleavage (deprotection) of the PTC-Phe group.

After completion (15 min), the product H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Pal-γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH was obtained and purified by preparative HPLC followed by lyophilization of the pure fractions.

In a likewise manner, Semaglutide was synthesized from the precursor PTC-Phe-$^1$His-$^2$Aib-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH of Example 2 using 17-tert-butyl-carboxyheptadecanoyl-Glu-γ-AEEA-AEEA-OSu followed by TFA deprotection of the tBu and PTC-Phe-groups.

Example 4

Enzymatic Synthesis of the Liraglutide Precursor PTC-Xxx-Liraglutide-1-31-[$^{20}$Lys(Pal-γ-Glu)]-OH Using a 3-Mer+28-Mer Approach.

In an HPLC vial, 10 mg of PTC-Phe-$^1$His-$^2$Ala-$^3$Glu-OCam-Leu-OH and 10 mg of H-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Pal-γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH were dissolved in 475 μL water. To this mixture, 25 μL 1 M tricine buffer pH 9.0 was added and the pH was adjusted to 8.7 using a 3M NaOH solution. Subsequently, 10 μL of TCEP (tris(2-carboxyethyl)phosphine) solution (100 mg/mL in water) and 10 μL of the ligase solution (10 mg/mL) were added. The mixture was left to react at ambient temperature. Every 15 minutes, 10 μL of the reaction mixture was withdrawn and quenched in 980 μL 5 vol % MSA in acetonitrile/water (2/1, v/v) and analysed using LC-MS.

After 90 minutes all Cam-ester starting material had been consumed, and the product and amine 28-mer starting material peaks were integrated. The ligation product PTC-Phe-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Pal-γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH was 74 area % and the leftover H-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-17Gln-18Ala-19Ala-20Lys (Pal-γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH starting material was 26 area %.

The product PTC-Phe-Liraglutide-1-31-[$^{20}$Lys(Pal-γ-Glu)]-OH could be obtained by preparative HPLC followed by lyophilization of the pure fractions.

Following the reaction as described above, almost identical results were obtained using PTC-Xxx-$^1$His-$^2$Ala-$^3$Glu-OCam-Leu-OH, wherein Xxx=Tyr, Leu, or Val or using MTC-Phe-$^1$His-$^2$Ala-$^3$Glu-OCam-Leu-OH.

Example 5

Enzymatic Synthesis of the Semaglutide Precursor PTC-Phe-Semaglutide-1-31-[$^{20}$Lys(AEEA-AEEA-γ-Glu-N-17-Carboxyheptadecanoyl-OH)]—OH Using a 3-Mer+28-Mer Approach.

In an HPLC vial, 10 mg of PTC-Phe-$^1$His-$^2$Aib-$^3$Glu-OCam-Leu-OH and 10 mg of H-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(AEEA-AEEA-γ-Glu-N-17-carboxyheptadecanoyl-OH)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH were dissolved in 475 μL water. To this mixture, 25 μL 1M tricine buffer pH 9.0 was added and the pH was adjusted to 8.7 using a 3M NaOH solution. Subsequently, 10 μL of TCEP (tris(2-carboxyethyl)phosphine) solution (100 mg/mL in water) and 10 μL of the ligase solution (10 mg/mL) were added. The mixture was left to react at ambient temperature. Every 15 minutes, 10 μL of the reaction mixture was withdrawn and quenched in 980 μL 5 vol % MSA in acetonitrile/water (2/1, v/v) and analysed using LC-MS.

After 90 minutes all Cam-ester starting material had been consumed, and the product and amine 28-mer starting material peaks were integrated. The ligation product PTC-Phe-$^1$His-$^2$Aib-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(AEEA-AEEA-γ-Glu-N-17-carboxyheptadecanoyl-OH)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH was 86 area % and the leftover H-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(AEEA-AEEA-γ-Glu-N-17-carboxyheptadecanoyl-OH)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH starting material was 14 area %.

The product PTC-Phe-Semaglutide-1-31-[$^{20}$Lys(AEEA-AEEA-γ-Glu-N-17-carboxyheptadecanoyl-OH)]—OH could be obtained by preparative HPLC followed by lyophilization of the pure fractions.

Example 6

Synthesis of H-Liraglutide-1-31-[²⁰Lys(Pal-γ-Glu)]-OH Using the PTC-Phe-Liraglutide-1-31-[²⁰Lys(Pal-γ-Glu)]-OH Precursor from Example 4 and Synthesis of H-Semaglutide-1-31-[²⁰Lys(AEEA-AEEA-γ-Glu-N-17-carboxyheptadecanoyl-OH)]—OH Using the PTC-Phe-Semaglutide-1-31-[²⁰Lys(AEEA-AEEA-γ-Glu-N-17-carboxyheptadecanoyl-OH)]—OH Precursor from Example 5

10 mg of PTC-Phe-¹His-²Ala-³Glu-⁴Gly-⁵Thr-⁶Phe-⁷Thr-⁸Ser-⁹Asp-¹⁰Val-¹¹Ser-¹²Ser-¹³Tyr-¹⁴Leu-¹⁵Glu-¹⁶Gly-¹⁷Gln-¹⁸Ala-¹⁹Ala-²⁰Lys(Pal-γ-Glu)-²¹Glu-²²Phe-²³Ile-²⁴Ala-²⁵Trp-²⁶Leu-²⁷Val-²⁸Arg-²⁹Gly-³⁰Arg-³¹Gly-OH was dissolved 95 vol % trifluoroacetic acid in water for cleavage (deprotection) of the PTC-Phe group.

After completion (15 min), the product H-¹His-²Ala-³Glu-⁴Gly-⁵Thr-⁶Phe-⁷Thr-⁸Ser-⁹Asp-¹⁰Val-¹¹Ser-¹²Ser-¹³Tyr-¹⁴Leu-¹⁵Glu-¹⁶Gly-¹⁷Gln-¹⁸Ala-¹⁹Ala-²⁰Lys(Pal-γ-Glu)-²¹Glu-²²Phe-²³Ile-²⁴Ala-²⁵Trp-²⁶Leu-²⁷Val-²⁸Arg-²⁹Gly-³⁰Arg-³¹Gly-OH was obtained and purified by preparative HPLC followed by lyophilization of the pure fractions.

In a likewise manner, Semaglutide was synthesized from the precursor PTC-Phe-¹His-²Aib-³Glu-⁴Gly-⁵Thr-⁶Phe-⁷Thr-⁸Ser-⁹Asp-¹⁰Val-¹¹Ser-¹²Ser-¹³Tyr-¹⁴Leu-¹⁵Glu-¹⁶Gly-¹⁷Gln-¹⁸Ala-¹⁹Ala-²⁰Lys(AEEA-AEEA-γ-Glu-N-17-carboxyheptadecanoyl-OH)-²¹Glu-²²Phe-²³Ile-²⁴Ala-²⁵Trp-²⁶Leu-²⁷Val-²⁸Arg-²⁹Gly-³⁰Arg-³¹Gly-OH.

Comparative Example 7

Synthesis of PTC-Phe-Semaglutide-1-31-OH Using Alternative Coupling Positions Several different coupling positions were investigated using the conditions of Example 1.

1. A 3-mer+28-mer approach: H-¹His-²Aib-³Glu-OCam-Leu-OH+H-⁴Gly-⁵Thr-⁶Phe-⁷Thr-⁸Ser-⁹Asp-¹⁰Val-¹¹Ser-¹²Ser-¹³Tyr-¹⁴Leu-¹⁵Glu-¹⁶Gly-¹⁷Gln-¹⁸Ala-¹⁹Ala-²⁰Lys-²¹Glu-²²Phe-²³Ile-²⁴Ala-²⁵Trp-²⁶Leu-²⁷Val-²⁸Arg-²⁹Gly-³⁰Arg-³¹Gly-OH. The coupling failed.

2. A 4-mer+27-mer approach: PTC-Phe-¹His-²Aib-³Glu-⁴Gly-OCam-Leu-OH+H-⁵Thr-⁶Phe-⁷Thr-⁸Ser-⁹Asp-¹⁰Val-¹¹Ser-¹²Ser-¹³Tyr-¹⁴Leu-¹⁵Glu-¹⁶Gly-¹⁷Gln-¹⁸Ala-¹⁹Ala-²⁰Lys-²¹Glu-²²Phe-²³Ile-²⁴Ala-²⁵Trp-²⁶Leu-²⁷Val-²⁸Arg-²⁹Gly-³⁰Arg-³¹Gly-OH. The coupling failed.

3. A 5-mer+26-mer approach: PTC-Phe-¹His-²Aib-³Glu-⁴Gly-⁵Thr-OCam-Leu-OH+H-⁶Phe-⁷Thr-⁸Ser-⁹Asp-¹⁰Val-¹¹Ser-¹²Ser-¹³Tyr-¹⁴Leu-¹⁵Glu-¹⁶Gly-¹⁷Gln-¹⁸Ala-¹⁹Ala-²⁰Lys-²¹Glu-²²Phe-²³Ile-²⁴Ala-²⁵Trp-²⁶Leu-²⁷Val-²⁸Arg-²⁹Gly-³⁰Arg-³¹Gly-OH. The coupling failed.

4. A 6-mer+25-mer approach: PTC-Phe-¹His-²Aib-³Glu-⁴Gly-⁵Thr-⁶Phe-OCam-Leu-OH+H-⁷Thr-⁸Ser-⁹Asp-¹⁰Val-¹¹Ser-¹²Ser-¹³Tyr-¹⁴Leu-¹⁵Glu-¹⁶Gly-¹⁷Gln-¹⁸Ala-¹⁹Ala-²⁰Lys-²¹Glu-²²Phe-²³Ile-²⁴Ala-²⁵Trp-²⁶Leu-²⁷Val-²⁸Arg-²⁹Gly-³⁰Arg-³¹Gly-OH. The coupling failed.

```
SEQUENCES
SEQ ID NO 1: wild type gene encoding for
subtilisin BPN' amino acids -107 to 275
ENA|K02496|K02496.1 B. Subtilisin BPN'
Bacillus amyloliquefaciens
GTGAGAGGCAAAAAAGTATGGATCAGTTTGCTGTTTGCTTTAGCGT

TAATCTTTACGATGGCGTTCGGCAGCACATCCTCTGCCCAGGCGGC

AGGGAAATCAAACGGGGAAAAGAAATATATTGTCGGGTTTAAACAG

ACAATGAGCACGATGAGCGCCGCTAAGAAGAAAGATGTCATTTCTG

AAAAAGGCGGGAAAGTGCAAAAGCAATTCAAATATGTAGACGCAGC

TTCAGCTACATTAAACGAAAAAGCTGTAAAAGAATTGAAAAAAGAC

CCGAGCGTCGCTTACGTTGAAGAAGATCACGTAGCACATGCGTACG

CGCAGTCCGTGCCTTACGGCGTATCACAAATTAAAGCCCCTGCTCT

GCACTCTCAAGGCTACACTGGATCAAATGTTAAAGTAGCGGTTATC

GACAGCGGTATCGATTCTTCTCATCCTGATTTAAAGGTAGCAGGCG

GAGCCAGCATGGTTCCTTCTGAAACAAATCCTTTCCAAGACAACAA

CTCTCACGGAACTCACGTTGCCGGCACAGTTGCGGCTCTTAATAAC

TCAATCGGTGTATTAGGCGTTGCGCCAAGCGCATCACTTTACGCTG

TAAAAGTTCTCGGTGCTGACGGTTCCGGCCAATACAGCTGGATCAT

TAACGGAATCGAGTGGGCGATCGCAAACAATATGGACGTTATTAAC

ATGAGCCTCGGCGGACCTTCTGGTTCTGCTGCTTTAAAAGCGGCAG

TTGATAAAGCCGTTGCATCCGGCGTCGTAGTCGTTGCGGCAGCCGG

TAACGAAGGCACTTCCGGCAGCTCAAGCACAGTGGGCTACCCTGGT

AAATACCCTTCTGTCATTGCAGTAGGCGCTGTTGACAGCAGCAACC

AAAGAGCATCTTTCTCAAGCGTAGGACCTGAGCTTGATGTCATGGC

ACCTGGCGTATCTATCCAAAGCACGCTTCCTGGAAACAAATACGGG

GCGTACAACGGTACGTCAATGGCATCTCCGCACGTTGCCGGAGCGG

CTGCTTTGATTCTTTCTAAGCACCCGAACTGGACAAACACTCAAGT

CCGCAGCAGTTTAGAAAACACCACTACAAAACTTGGTGATTCTTTC

TACTATGGAAAAGGGCTGATCAACGTACAGGCGGCAGCTCAGTAA

SEQ ID NO 2: wild type subtilisin BPN' (mature)
>SUBT_BACAM Subtilisin BPN' Bacillus
amyloliquefaciens mature 1 to 275
>sp|P00782|108-382
AQSVPYGVSQIKAPALHSQGYTGSNVKVAVIDSGIDSSHPDLKVAG

GASMVPSETNPFQDNNSHGTHVAGTVAALNNSIGVLGVAPSASLYA

VKVLGADGSGQYSWIINGIEWAIANNMDVINMSLGGPSGSAALKAA

VDKAVASGVVVVAAAGNEGTSGSSSTVGYPGKYPSVIAVGAVDSSN

QRASFSSVGPELDVMAPGVSIQSTLPGNKYGAYNGTSMASPHVAGA

AALILSKHPNWTNTQVRSSLENTTTKLGDSFYYGKGLINVQAAAQ

SEQ ID NO 3: subtilisin BPN' variant having
mutations Q2K, S3C, P5S, S9A, I31L, K43N, M50F,
N62A, A73L, A75-83, E156N, G166E, G169A, S188P,
F189W, Q206C, N212G, Y217H, N218D, S221C,
M222P, P225N, T254A, and Q271E and a His tag
AKCVSYGVAQIKAPALHSQGYTGSNVKVAVLDSGIDSSHPDLNVAG

GASFVPSETNPFQDNASHGTHVAGTVLAVAPSASLYAVKVLGADGS

GQYSWIINGIEWAIANNMDVINMSLGGPSGSAALKAAVDKAVASGV

VVVAAAGNNGTSGSSSTVEYPAKYPSVIAVGAVDSSNQRAPWSSVG

PELDVMAPGVSICSTLPGGKYGAHDGTCPASNHVAGAAALILSKHP

NWTNTQVRSSLENTATKLGDSFYYGKGLINVEAAAQHHHHHH
```

The invention claimed is:

1. A method for preparing a coupling product comprising the sequence $P_q$-$W_v$-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly, comprising enzymatically coupling (a) a peptide C-terminal ester or thioester comprising a first peptide fragment represented by the formula $P_q$-$W_v$-His-X-Glu-(thio)ester; and (b) a peptide nucleophile, having an N-terminally unprotected amine, comprising a second peptide fragment, comprising the sequence H-Gly-Thr-Phe-Thr-Ser-Asp- Val-Ser-Ser-Tyr-Leu-Glu-Gly-Gln-Ala-Ala-Y-Glu-Phe-Ile-Ala-Trp-Leu-Val-Z-Gly-Arg-Gly wherein P represents a protective group at the N-terminal α-amino function of said peptide C-terminal ester or thioester and q is an integer having a value of 1 or 0;

W represents one or more α-amino acid residues, which may be the same or different and v is an integer having a value of 1, 2 or 3 representing the number of α-amino acid residues W;

X is Ala or an α-amino-isobutyric acid unit (Aib);

Y is Lys, which Lys has a free side-chain ε-amino group or a side-chain ε-amino group that is protected with a protective group or a side-chain ε-amino group that is functionalized with an amino acid or a functional group selected from the group consisting of γ-Glu-OH, Pal-γ-Glu-OH, AEEA-AEEA-γ-Glu-OH and AEEA-AEEA-γ-Glu-N-17-carboxyheptadecanoyl-OH, wherein Pal is palmitoyl and AEEA-AEEA is 2-[2-(2-aminoethoxy)ethoxy]acetyl-2-[2-(2-aminoethoxy)ethoxy]acetyl; and Z is Arg or Lys;

which enzymatic coupling is catalysed by a ligase, wherein the ligase is a subtilisin BPN' variant or a homologue thereof, which comprises the following mutations compared to subtilisin BPN' represented by SEQ ID NO: 2 or a homologue sequence thereof:

a deletion of the amino acids corresponding to positions 75-83;

a mutation at the amino acid position corresponding to S221, the mutation being S221C or S221 selenocysteine;

wherein the amino acid positions are defined according to the sequence of subtilisin BPN' represented by SEQ ID NO: 2.

2. The method according to claim 1, further comprising removing the 'P$_q$-W$_v$' moiety from the product comprising the sequence P$_q$-W$_v$-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly such as to obtain a peptide with the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly, wherein P, q, v, W, X, Y, and Z are as defined in claim 1.

3. The method according to claim 2, wherein v is 1.

4. The method according to claim 2, wherein the W adjacent to the His is selected from the group consisting of Phe, Leu, Ile, Val, Ala, Tyr, Met, Pro and Trp.

5. The method according to claim 2, wherein P represents a substituted thiocarbamoyl group.

6. The method according to claim 2, wherein Semaglutide is synthesized.

7. The method according to claim 6, comprising enzymatically coupling:

(a) the peptide C-terminal ester or thioester represented by the formula Pq-Wv-His-Aib-Glu-(thio)ester, and (b) the peptide nucleophile comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Arg-Gly-Arg-Gly, wherein Y is Lys(AEEA-AEEA-γ-Glu-N-17-carboxyheptadecanoyl-OH).

8. The method according to claim 6, comprising enzymatically coupling:

(a) the peptide C-terminal ester or thioester represented by the formula P-W$_v$-His-Aib-Glu-(thio)ester, and (b) the peptide nucleophile comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Arg-Gly-Arg-Gly, wherein Y is Lys(AEEA-AEEA-γ-Glu-OH), thereby forming a peptide represented by the formula P-W$_v$-His-Aib-Glu-Gly-Thr-Phe-Thr-Ser-Asp-Val-Ser-Ser-Tyr-Leu-Glu-Gly-Gln-Ala-Ala-Lys(AEEA-AEEA-γ-Glu-OH)-Glu-Phe-Ile-Ala-Trp-Leu-Val-Arg-Gly-Arg-Gly, and then providing the Lys(AEEA-AEEA-γ-Glu-OH) with a 17-carboxyheptadecanoyl group to obtain P-W$_v$-His-Aib-Glu-Gly-Thr-Phe-Thr-Ser-Asp-Val-Ser-Ser-Tyr-Leu-Glu-Gly-Gln-Ala-Ala-Lys(AEEA-AEEA-γ-Glu-N-17-carboxyheptadecanoyl-OH)-Glu-Phe-Ile-Ala-Trp-Leu-Val-Arg-Gly-Arg-Gly.

9. The method according to claim 6, comprising enzymatically coupling:

(a) the peptide C-terminal ester or thioester represented by the formula P$_q$-W$_v$-His-Aib-Glu-(thio)ester, and (b) the peptide nucleophile comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Arg-Gly-Arg-Gly, wherein Y is a lysine residue having a free or protected side-chain ε-amino group, and thereafter providing the Lys side-chain ε-amino group with a AEEA-AEEA-γ-Glu-N-17-carboxyheptadecanoyl-OH group.

10. The method according to claim 2, wherein Liraglutide is synthesized.

11. The method according to claim 10, comprising enzymatically coupling:

(a) the peptide C-terminal ester or thioester represented by the formula P$_q$-W$_v$-His-Ala-Glu-(thio)ester, and (b) the peptide nucleophile comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Arg-Gly-Arg-Gly, wherein Y is Lys(Pal-γ-Glu-OH).

12. The method according to claim 10, comprising enzymatically coupling:

(a) the peptide C-terminal ester or thioester represented by the formula P-W$_v$-His-Ala-Glu(thio)ester, and (b) the peptide nucleophile comprising the sequence H-Gly-Thr-Phe-Thr-Ser-Asp-Val-Ser-Ser-Tyr-Leu-Glu-Gly-Gln-Ala-Ala-Lys(γ-Glu-OH)-Glu-Phe-Ile-Ala-Trp-Leu-Val-Arg-Gly-Arg-Gly;

thereby obtaining a peptide represented by the formula P-W$_v$-His-Ala-Glu-Gly-Thr-Phe-Thr-Ser-Asp-Val-Ser-Ser-Tyr-Leu-Glu-Gly-Gln-Ala-Ala-Lys(γ-Glu-OH)-Glu-Phe-Ile-Ala-Trp-Leu-Val-Arg-Gly-Arg-Gly, and then providing said Lys(γ-Glu-OH) of said peptide with a palmitoyl group (Pal), to obtain P-W$_v$-His-Ala-Glu-Gly-Thr-Phe-Thr-Ser-A sp-Val-Ser-Ser-Tyr-Leu-Glu-Gly-Gln-Ala-Ala-Lys(Pal-γ-Glu-OH)-Glu-Phe-Ile-Ala-Trp-Leu-Val-Arg-Gly-Arg-Gly.

13. The method according to claim 10, comprising enzymatically coupling:

(a) the peptide C-terminal ester or thioester represented by formula P$_q$-W$_v$-His-Ala-Glu-(thio)ester, and (b) the peptide nucleophile comprising the sequence H-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Arg-Gly-Arg-Gly, wherein Y is a lysine residue having a free or protected side-chain ε-amino group; and thereafter providing said side-chain ε-amino group with Pal-γ-Glu-OH.

14. The method according to claim 2, wherein GLP-1 is synthesized.

15. The method according to claim 1, wherein the ligase comprises 1-13 further mutations selected from the group consisting of Q2K, S3C, P5S, S9A, I31L, K43N, M50F, A73L, S188P, Q206C, N212G, T254A and Q271E.

16. The method according to claim 15, wherein the ligase is the subtilisin BPN' variant with SEQ ID NO: 3, comprising the mutations Q2K, S3C, P5S, S9A, I31L, K43N, M50F, N62A, A73L, 475-83, E156N, G166E, G169A, S188P, F189W, Q206C, N212G, Y217H, N218D, S221C, M222P, P225N, T254A, and Q271E, or a homologue thereof comprising the mutations and having at least 80% sequence identity with SEQ ID NO: 3.

17. The method according to claim 1, wherein the subtilisin BPN' variant or a homologue thereof further comprises a mutation at the amino acid position corresponding to P225.

18. The method according to claim 15, wherein the ligase comprises 9-11 further mutations, wherein at least ten of said mutations are selected from the group consisting of Q2K, S3C, P5S, S9A, I31L, K43N, M50F, A73L, S188P, Q206C, N212G, T254A and Q271E.

19. The method according to claim 16, wherein the homologue has at least 90% sequence identity with SEQ ID NO: 2.

20. The method according to claim 1, wherein the S/H ratio is larger than 1.

* * * * *

SEQUENCE LISTING

<160> NUMBER OF SEQ ID NOS: 10

<210> SEQ ID NO 1
<211> LENGTH: 1149
<212> TYPE: DNA
<213> ORGANISM: Bacillus amyloliquefaciens
<220> FEATURE:
<221> NAME/KEY: CDS
<222> LOCATION: (322)..(1149)

<400> SEQUENCE: 1

```
gtgagaggca aaaagtatg gatcagtttg ctgtttgctt tagcgttaat ctttacgatg      60
gcgttcggca gcacatcctc tgcccaggcg gcagggaaat caaacgggga aagaaatat    120 attgtcgggt ttaaacagac aatgagcacg atgagcgccg ctaagaagaa agatgtcatt   180
tctgaaaaag gcgggaaagt gcaaaagcaa ttcaaatatg tagacgcagc ttcagctaca   240
ttaaacgaaa aagctgtaaa agaattgaaa aagacccga gcgtcgctta cgttgaagaa    300
gatcacgtag cacatgcgta c gcg cag tcc gtg cct tac ggc gta tca caa     351
                        Ala Gln Ser Val Pro Tyr Gly Val Ser Gln
                          1               5                    10 att aaa gcc cct gct ctg cac tct caa ggc tac act gga tca aat gtt    399
Ile Lys Ala Pro Ala Leu His Ser Gln Gly Tyr Thr Gly Ser Asn Val
                 15                  20                  25 aaa gta gcg gtt atc gac agc ggt atc gat tct tct cat cct gat tta    447
Lys Val Ala Val Ile Asp Ser Gly Ile Asp Ser Ser His Pro Asp Leu
         30                  35                  40 aag gta gca ggc gga gcc agc atg gtt cct tct gaa aca aat cct ttc    495
Lys Val Ala Gly Gly Ala Ser Met Val Pro Ser Glu Thr Asn Pro Phe
     45                  50                  55 caa gac aac aac tct cac gga act cac gtt gcc ggc aca gtt gcg gct    543
Gln Asp Asn Asn Ser His Gly Thr His Val Ala Gly Thr Val Ala Ala
 60                  65                  70 ctt aat aac tca atc ggt gta tta ggc gtt gcg cca agc gca tca ctt    591
Leu Asn Asn Ser Ile Gly Val Leu Gly Val Ala Pro Ser Ala Ser Leu
75                  80                  85                  90 tac gct gta aaa gtt ctc ggt gct gac ggt tcc ggc caa tac agc tgg    639
Tyr Ala Val Lys Val Leu Gly Ala Asp Gly Ser Gly Gln Tyr Ser Trp
                 95                 100                 105 atc att aac gga atc gag tgg gcg atc gca aac aat atg gac gtt att    687
Ile Ile Asn Gly Ile Glu Trp Ala Ile Ala Asn Asn Met Asp Val Ile
             110                 115                 120 aac atg agc ctc ggc gga cct tct ggt tct gct gct tta aaa gcg gca    735
Asn Met Ser Leu Gly Gly Pro Ser Gly Ser Ala Ala Leu Lys Ala Ala
         125                 130                 135 gtt gat aaa gcc gtt gca tcc ggc gtc gta gtc gtt gcg gca gcc ggt    783
Val Asp Lys Ala Val Ala Ser Gly Val Val Val Ala Ala Ala Gly
     140                 145                 150 aac gaa ggc act tcc ggc agc tca agc aca gtg ggc tac cct ggt aaa    831
Asn Glu Gly Thr Ser Gly Ser Ser Ser Thr Val Gly Tyr Pro Gly Lys
155                 160                 165                 170 tac cct tct gtc att gca gta ggc gct gtt gac agc agc aac caa aga    879
Tyr Pro Ser Val Ile Ala Val Gly Ala Val Asp Ser Ser Asn Gln Arg
                 175                 180                 185 gca tct ttc tca agc gta gga cct gag ctt gat gtc atg gca cct ggc    927
Ala Ser Phe Ser Ser Val Gly Pro Glu Leu Asp Val Met Ala Pro Gly
             190                 195                 200 gta tct atc caa agc acg ctt cct gga aac aaa tac ggg gcg tac aac    975
Val Ser Ile Gln Ser Thr Leu Pro Gly Asn Lys Tyr Gly Ala Tyr Asn
         205                 210                 215
```

-continued

| | | |
|---|---|---|
| ggt acg tca atg gca tct ccg cac gtt gcc gga gcg gct gct ttg att<br>Gly Thr Ser Met Ala Ser Pro His Val Ala Gly Ala Ala Ala Leu Ile<br>220                         225                                 230 | 1023 | |
| ctt tct aag cac ccg aac tgg aca aac act caa gtc cgc agc agt tta<br>Leu Ser Lys His Pro Asn Trp Thr Asn Thr Gln Val Arg Ser Ser Leu<br>235                         240                         245                        250 | 1071 | |
| gaa aac acc act aca aaa ctt ggt gat tct ttc tac tat gga aaa ggg<br>Glu Asn Thr Thr Thr Lys Leu Gly Asp Ser Phe Tyr Tyr Gly Lys Gly<br>                        255                         260                        265 | 1119 | |
| ctg atc aac gta cag gcg gca gct cag taa<br>Leu Ile Asn Val Gln Ala Ala Ala Gln<br>270                         275 | 1149 | |

<210> SEQ ID NO 2
<211> LENGTH: 275
<212> TYPE: PRT
<213> ORGANISM: Bacillus amyloliquefaciens

<400> SEQUENCE: 2

Ala Gln Ser Val Pro Tyr Gly Val Ser Gln Ile Lys Ala Pro Ala Leu
1                  5                       10                    15

His Ser Gln Gly Tyr Thr Gly Ser Asn Val Lys Val Ala Val Ile Asp
                  20                       25                      30

Ser Gly Ile Asp Ser Ser His Pro Asp Leu Lys Val Ala Gly Gly Ala
         35                      40                       45

Ser Met Val Pro Ser Glu Thr Asn Pro Phe Gln Asp Asn Asn Ser His
50                        55                       60

Gly Thr His Val Ala Gly Thr Val Ala Ala Leu Asn Asn Ser Ile Gly
65                        70                       75                    80

Val Leu Gly Val Ala Pro Ser Ala Ser Leu Tyr Ala Val Lys Val Leu
                  85                       90                      95

Gly Ala Asp Gly Ser Gly Gln Tyr Ser Trp Ile Ile Asn Gly Ile Glu
                 100                      105                     110

Trp Ala Ile Ala Asn Asn Met Asp Val Ile Asn Met Ser Leu Gly Gly
             115                      120                     125

Pro Ser Gly Ser Ala Ala Leu Lys Ala Ala Val Asp Lys Ala Val Ala
130                       135                     140

Ser Gly Val Val Val Ala Ala Ala Gly Asn Glu Gly Thr Ser Gly
145                       150                     155                    160

Ser Ser Ser Thr Val Gly Tyr Pro Gly Lys Tyr Pro Ser Val Ile Ala
                 165                      170                     175

Val Gly Ala Val Asp Ser Ser Asn Gln Arg Ala Ser Phe Ser Ser Val
             180                      185                     190

Gly Pro Glu Leu Asp Val Met Ala Pro Gly Val Ser Ile Gln Ser Thr
         195                      200                     205

Leu Pro Gly Asn Lys Tyr Gly Ala Tyr Asn Gly Thr Ser Met Ala Ser
210                       215                     220

Pro His Val Ala Gly Ala Ala Ala Leu Ile Leu Ser Lys His Pro Asn
225                       230                     235                    240

Trp Thr Asn Thr Gln Val Arg Ser Ser Leu Glu Asn Thr Thr Thr Lys
             245                      250                     255

Leu Gly Asp Ser Phe Tyr Tyr Gly Lys Gly Leu Ile Asn Val Gln Ala
         260                      265                     270

Ala Ala Gln
275

-continued

```
<210> SEQ ID NO 3
<211> LENGTH: 272
<212> TYPE: PRT
<213> ORGANISM: Artificial Sequence
<220> FEATURE:
<223> OTHER INFORMATION: mutant subtilisin B
<220> FEATURE:
<221> NAME/KEY: MISC_FEATURE
<222> LOCATION: (267)..(272)
<223> OTHER INFORMATION: His-tag

<400> SEQUENCE: 3
```

Ala Lys Cys Val Ser Tyr Gly Val Ala Gln Ile Lys Ala Pro Ala Leu
1               5                   10                  15

His Ser Gln Gly Tyr Thr Gly Ser Asn Val Lys Val Ala Val Leu Asp
            20                  25                  30

Ser Gly Ile Asp Ser Ser His Pro Asp Leu Asn Val Ala Gly Gly Ala
        35                  40                  45

Ser Phe Val Pro Ser Glu Thr Asn Pro Phe Gln Asp Asn Ala Ser His
    50                  55                  60

Gly Thr His Val Ala Gly Thr Val Leu Ala Val Ala Pro Ser Ala Ser
65                  70                  75                  80

Leu Tyr Ala Val Lys Val Leu Gly Ala Asp Gly Ser Gly Gln Tyr Ser
                85                  90                  95

Trp Ile Ile Asn Gly Ile Glu Trp Ala Ile Ala Asn Asn Met Asp Val
            100                 105                 110

Ile Asn Met Ser Leu Gly Gly Pro Ser Gly Ser Ala Ala Leu Lys Ala
        115                 120                 125

Ala Val Asp Lys Ala Val Ala Ser Gly Val Val Val Ala Ala Ala
    130                 135                 140

Gly Asn Asn Gly Thr Ser Gly Ser Ser Ser Thr Val Glu Tyr Pro Ala
145                 150                 155                 160

Lys Tyr Pro Ser Val Ile Ala Val Gly Ala Val Asp Ser Ser Asn Gln
                165                 170                 175

Arg Ala Pro Trp Ser Ser Val Gly Pro Glu Leu Asp Val Met Ala Pro
            180                 185                 190

Gly Val Ser Ile Cys Ser Thr Leu Pro Gly Gly Lys Tyr Gly Ala His
        195                 200                 205

Asp Gly Thr Cys Pro Ala Ser Asn His Val Ala Gly Ala Ala Ala Leu
    210                 215                 220

Ile Leu Ser Lys His Pro Asn Trp Thr Asn Thr Gln Val Arg Ser Ser
225                 230                 235                 240

Leu Glu Asn Thr Ala Thr Lys Leu Gly Asp Ser Phe Tyr Tyr Gly Lys
                245                 250                 255

Gly Leu Ile Asn Val Glu Ala Ala Gln His His His His His
            260                 265                 270

```
<210> SEQ ID NO 4
<211> LENGTH: 31
<212> TYPE: PRT
<213> ORGANISM: Artificial Sequence
<220> FEATURE:
<223> OTHER INFORMATION: consensus peptide fragment
<220> FEATURE:
<221> NAME/KEY: VARIANT
<222> LOCATION: (2)..(2)
<223> OTHER INFORMATION: may also be an alpha-amino-isobutyric acid unit
```

```
<220> FEATURE:
<221> NAME/KEY: MISC_FEATURE
<222> LOCATION: (20)..(20)
<223> OTHER INFORMATION: Lys has a free side-chain epsilon-amino group
      or  a  side-chain epsilon-amino group that is protected with a
      protective group or a side-chain epsilon-amino group that is
      functionalised with an amino acid or another functional group
<220> FEATURE:
<221> NAME/KEY: VARIANT
<222> LOCATION: (28)..(28)
<223> OTHER INFORMATION: may also be K

<400> SEQUENCE: 4

His Ala Glu Gly Thr Phe Thr Ser Asp Val Ser Ser Tyr Leu Glu Gly
1               5                   10                  15

Asn Ala Ala Lys Glu Phe Ile Ala Trp Leu Val Arg Gly Arg Gly
            20                  25                  30

<210> SEQ ID NO 5
<211> LENGTH: 31
<212> TYPE: PRT
<213> ORGANISM: Homo sapiens

<400> SEQUENCE: 5

His Ala Glu Gly Thr Phe Thr Ser Asp Val Ser Ser Tyr Leu Glu Gly
1               5                   10                  15

Asn Ala Ala Lys Glu Phe Ile Ala Trp Leu Val Lys Gly Arg Gly
            20                  25                  30

<210> SEQ ID NO 6
<211> LENGTH: 31
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Lys is Lys(Pal-gamma-Glu)-
<220> FEATURE:
<221> NAME/KEY: MOD_RES
<222> LOCATION: (20)..(20)
<223> OTHER INFORMATION: Lys is Lys(Pal-gamma-Glu)

<400> SEQUENCE: 6

His Ala Glu Gly Thr Phe Thr Ser Asp Val Ser Ser Tyr Leu Glu Gly
1               5                   10                  15

Asn Ala Ala Lys Glu Phe Ile Ala Trp Leu Val Lys Gly Arg Gly
            20                  25                  30

<210> SEQ ID NO 7
<211> LENGTH: 31
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: bAib
<220> FEATURE:
<221> NAME/KEY: MOD_RES
<222> LOCATION: (20)..(20)
<223> OTHER INFORMATION: Lys is
      Lys(AEEA-AEEA-gamma-Glu-17-carboxyheptadecanoyl)

<400> SEQUENCE: 7

His Ala Glu Gly Thr Phe Thr Ser Asp Val Ser Ser Tyr Leu Glu Gly
1               5                   10                  15

Asn Ala Ala Lys Glu Phe Ile Ala Trp Leu Val Lys Gly Arg Gly
            20                  25                  30
```

```
<210> SEQ ID NO 8
<211> LENGTH: 4
<212> TYPE: PRT
<213> ORGANISM: Artificial Sequence
<220> FEATURE:
<223> OTHER INFORMATION: coupling reagent for production of liraglutide

<400> SEQUENCE: 8

His Ala Glu Gly
1

<210> SEQ ID NO 9
<211> LENGTH: 27
<212> TYPE: PRT
<213> ORGANISM: Artificial Sequence
<220> FEATURE:
<223> OTHER INFORMATION: coupling reagent for production of liraglutide
<220> FEATURE:
<221> NAME/KEY: MOD_RES
<222> LOCATION: (20)..(20)
<223> OTHER INFORMATION: Lys is Lys(Pal-Glu-OX) in which X is H or
      protective group

<400> SEQUENCE: 9

Thr Phe Thr Ser Asp Val Ser Ser Tyr Leu Glu Gly Asn Ala Ala Lys
1               5                   10                  15

Glu Phe Ile Ala Trp Leu Val Arg Gly Arg Gly
            20                  25

<210> SEQ ID NO 10
<211> LENGTH: 32
<212> TYPE: PRT
<213> ORGANISM: Artificial Sequence
<220> FEATURE:
<223> OTHER INFORMATION: coupling product
<220> FEATURE:
<221> NAME/KEY: MOD_RES
<222> LOCATION: (1)..(1)
<223> OTHER INFORMATION: may have a protective grooup
<220> FEATURE:
<221> NAME/KEY: MISC_FEATURE
<222> LOCATION: (1)..(1)
<223> OTHER INFORMATION: one or more alpha-amino acids
<220> FEATURE:
<221> NAME/KEY: MOD_RES
<222> LOCATION: (3)..(3)
<223> OTHER INFORMATION: May be alpha-amino-isobutyric acid
<220> FEATURE:
<221> NAME/KEY: MOD_RES
<222> LOCATION: (21)..(21)
<223> OTHER INFORMATION: May have a free side-chain epsilon-amino group
      or  a  side-chain epsilon-amino group that is protected with a
      protective group or a side-chain epsilon-amino group that is
      functionalised with an amino acid or another functional group
<220> FEATURE:
<221> NAME/KEY: VARIANT
<222> LOCATION: (29)..(29)
<223> OTHER INFORMATION: May be Lys

<400> SEQUENCE: 10

Xaa His Ala Glu Gly Thr Phe Thr Ser Asp Val Ser Ser Tyr Leu Glu
1               5                   10                  15

Gly Asn Ala Ala Lys Glu Phe Ile Ala Trp Leu Val Arg Gly Arg Gly
            20                  25                  30
```